(12) United States Patent
Oka et al.

(10) Patent No.: US 6,482,163 B2
(45) Date of Patent: Nov. 19, 2002

(54) POSTOPERATIVE-CONDITION EVALUATING APPARATUS

(75) Inventors: Tohru Oka, Ichinomiya (JP); Takashi Nomura, Komaki (JP)

(73) Assignee: Colin Corporation, Komaki (JP)

( * ) Notice: Subject to any disclaimer, the term of this patent is extended or adjusted under 35 U.S.C. 154(b) by 40 days.

(21) Appl. No.: 09/822,347

(22) Filed: Apr. 2, 2001

(65) Prior Publication Data

US 2002/0013533 A1 Jan. 31, 2002

(30) Foreign Application Priority Data

Jul. 26, 2000 (JP) ........................................ 2000-225554

(51) Int. Cl.[7] ........................ A61B 5/021; A61B 5/0245
(52) U.S. Cl. ........................ 600/481; 600/300; 600/485; 600/509
(58) Field of Search ............................. 600/481, 300, 600/500–504, 485, 509

(56) References Cited

U.S. PATENT DOCUMENTS

| 5,752,913 | A | * | 5/1998 | Oka | 600/300 |
| 5,772,601 | A | * | 6/1998 | Oka et al. | 600/495 |
| 5,830,149 | A | * | 11/1998 | Oka et al. | 600/500 |
| 5,836,887 | A | * | 11/1998 | Oka et al. | 600/494 |
| 6,177,940 | B1 | * | 1/2001 | Bond et al. | 600/300 |
| 6,361,501 | B1 | * | 3/2002 | Amano et al. | 600/500 |

* cited by examiner

Primary Examiner—Joseph Pelham
(74) Attorney, Agent, or Firm—Oliff & Berridge, PLC

(57) ABSTRACT

An apparatus for evaluating a degree of recovery of a living subject from a surgical operation which the subject has undergone, the apparatus including a circulatory-organ-relating-information obtaining device for iteratively obtaining, after the operation, a piece of circulatory-organ-relating information relating to a circulatory organ of the subject, and a recovery-degree evaluating device for evaluating the degree of recovery of the subject, based on at least one piece of circulatory-organ-relating information obtained by the circulatory-organ-relating-information obtaining device.

12 Claims, 13 Drawing Sheets

POSTOPERATIVE-CONDITION EVALUATING APPARATUS

BACKGROUND OF THE INVENTION

1. Field of the Invention

The present invention relates to an apparatus for evaluating a degree of recovery of a living subject from a surgical operation.

2. Related Art Statement

A living subject who has undergone a surgical operation is monitored, in, e.g., a recovery room, with respect to blood pressure, heart rate, blood oxygen saturation, etc. Based on the blood pressure, heart rate, and/or blood oxygen saturation being monitored, a doctor judges, from his or her experience, whether the subject has recovered from the surgical operation and, if it is judged that the subject has recovered, then the subject is moved to a general ward. The judgment made in this manner about the degree of recovery of the subject from the operation is more or less unclear, but it is not problematic so long as the subject is kept in hospital.

Meanwhile, recently, a day operation has become popular. The day operation means that in a single day a patient undergoes a surgical operation and goes home. If a judgment made by a doctor about a postoperative condition of a patient who has undergone a day operation is unclear, then the condition of the patient may become worse after the patient goes home. After the patient goes home, the doctor cannot do a quick treatment on the patient. Thus, it has been needed to objectively or quantitatively evaluate a postoperative condition of a living subject.

SUMMARY OF THE INVENTION

It is therefore an object of the present invention to provide an apparatus which can objectively and accurately evaluate a degree of recovery of a living subject from a surgical operation.

To this end, the Inventors have carried out an extensive study and have found that information relating to the circulatory organ of a living subject who has undergone a surgical operation largely and randomly changes from its values before the operation, because of anesthesia or physical stimuli administered or applied to the subject during the operation. However, after the operation, the circulatory-organ-relating information will change toward its values before the operation. The Inventors have found such a phenomenon that the circulatory-organ-relating information obtained after the operation will become stable around a certain saturation value, and such a fact that the change of circulatory-organ-relating information obtained after the operation is closely related to the degree of recovery of the subject from the operation. The present invention has been developed based on those findings.

The above object has been achieved by the present invention. According to the present invention, there is provided an apparatus for evaluating a degree of recovery of a living subject from a surgical operation which the subject has undergone, the apparatus comprising a circulatory-organ-relating-information obtaining means for iteratively obtaining, after the operation, a piece of circulatory-organ-relating information relating to a circulatory organ of the subject; and a recovery-degree evaluating means for evaluating the degree of recovery of the subject, based on at least one piece of circulatory-organ-relating information obtained by the circulatory-organ-relating-information obtaining means.

In the present apparatus, the circulatory-organ-relating-information obtaining means iteratively obtains, after the surgical operation, a piece of circulatory-organ-relating information relating to the circulatory organ of the living subject, and the recovery-degree evaluating means evaluates the degree of recovery of the subject, based on one or more pieces of circulatory-organ-relating information obtained by the circulatory-organ-relating-information obtaining means. Thus, present apparatus can objectively and accurately evaluate the degree of recovery of the subject from the operation which the subject has undergone.

Peferably, the recovery-degree evaluating means comprises means for evaluating the degree of recovery of the subject, by judging whether a change of a plurality of pieces of circulatory-organ-relating information iteratively obtained by the circulatory-organ-relating-information obtaining means is smaller than a reference value and accordingly is stable. There is a phenomenon that the pieces of circulatory-organ-relating information iteratively obtained from the postoperative subject by the circulatory-organ-relating-information obtaining means change toward a saturation value and become stable around the same. Since the recovery-degree evaluating means evaluates the degree of recovery of the subject, by judging whether a change of the pieces of circulatory-organ-relating information is smaller than a reference value and accordingly is stable, the present apparatus can objectively and accurately evaluate the degree of recovery of the subject from the operation.

Preferably, the circulatory-organ-relating-information obtaining means comprises means for iteratively obtaining, as a piece of circulatory-organ-relating information, one selected from the group consisting of a blood pressure Value, a heart rate value, a magnitude of a fluctuation of blood pressure values, and a magnitude of a fluctuation of heart rate values. There is a phenomenon that the blood pressure values, heart rate values, magnitudes of fluctuation of blood pressure values, or magnitudes of fluctuation of heart rate values, iteratively obtained from the postoperative subject by the circulatory-organ-relating-information obtaining means change toward a saturation value and become stable around the same. Thus, the present apparatus can evaluate, based on a change of those values, the degree of recovery of the subject from the operation.

Preferably, the recovery-degree evaluating means comprises means for determining a saturation value based on a time-wise change of a plurality of pieces of circulatory-organ-relating information iteratively obtained by the circulatory-organ-relating-information obtaining means, means for determining, based on the saturation value, a reference value smaller than the saturation value, and means for evaluating the degree of recovery of the subject, by judging whether a piece of circulatory-organ-relating information obtained by the circulatory-organ-relating-information obtaining means is greater than the reference value. The pieces of circulatory-organ-relating information iteratively obtained from the postoperative subject by the circulatory-organ-relating-information obtaining means have a nature to change along a logarithmic curve, and accordingly can be expressed by a logarithmic function. Therefore, a saturation value of the information can be determined, for each living subject, based on a time-wise change of the information. Since the recovery-degree evaluating means evaluates the degree of recovery of the subject, by judging whether an actual piece of circulatory-organ-relating information is greater than the reference value lower than the saturation value, the present apparatus can accurately evaluate the degree of recovery of the subject, independent of individual differences of living subjects.

Preferably, the circulatory-organ-relating-information obtaining means comprises means for iteratively obtaining, as a piece of circulatory-organ-relating information, one selected from the group consisting of a magnitude of a low-frequency fluctuation of blood pressure values, and a ratio of one of a magnitude of a low-frequency fluctuation of heart rate values and a magnitude of a high-frequency fluctuation of the heart rate values to the other of the magnitude of low-frequency fluctuation of heart rate values and the magnitude of high-frequency fluctuation of heart rate values, and the recovery-degree evaluating means comprises means for evaluating the degree of recovery of the subject, by judging whether the one selected from the group is greater than a reference value. It is speculated that the magnitude of low-frequency fluctuation of blood pressure values of the subject, or the ratio of one of the magnitude of low-frequency fluctuation of heart rate values and the magnitude of high-frequency fluctuation of the heart rate values to the other of the magnitude of low-frequency fluctuation of heart rate values and the magnitude of high-frequency fluctuation of heart rate values faithfully reflects the activity of the sympathetic nerve system of the subject. Since the recovery-degree evaluating means evaluates the degree of recovery of the subject, by judging whether a blood pressure value or the ratio is greater than a reference value, the present apparatus can objectively and accurately evaluate the degree of recovery of the subject from the operation.

Preferably, the circulatory-organ-relating-information obtaining means comprises means for iteratively obtaining, as a piece of circulatory-organ-relating information, one selected from the group consisting of a frequency distribution of fluctuations of blood pressure values, and a frequency distribution of fluctuations of heart rate values, and means for determining a degree of sharpness of the one selected from the group, and the recovery-degree evaluating means comprises means for evaluating the degree of recovery of the subject, by judging whether the determined degree of sharpness is greater than a reference value. The sharpness-degree values of the frequency distribution of fluctuations of blood pressure values or the frequency distribution of fluctuations of heart rate values, iteratively obtained from the postoperative subject change toward a value before the operation. Since the recovery-degree evaluating means evaluates the degree of recovery of the subject, by judging whether a sharpness degree of the frequency distribution is greater than a reference value, the present apparatus can objectively and accurately evaluate the degree of recovery of the subject.

Preferably, the circulatory-organ-relating-information obtaining means comprises means for iteratively obtaining, as a piece of circulatory-organ-relating information, one selected from the group consisting of a frequency spectrum of fluctuations of blood pressure values, and a frequency spectrum of fluctuations of heart rate values, and means for determining a proportion of an interval fluctuation magnitude of the one selected from the group in a prescribed frequency interval, with respect to a whole fluctuation magnitude of the one selected from the group in a whole frequency range, and the recovery-degree evaluating means comprises means for evaluating the degree of recovery of the subject, by judging whether the determined proportion is greater than a reference value. The proportion of interval fluctuation magnitude of the frequency spectrum of fluctuations of blood pressure values or the frequency spectrum of fluctuations of heart rate values, iteratively obtained from the postoperative subject, change toward a value before the operation. Since the recovery-degree evaluating means evaluates the degree of recovery of the subject, by judging whether a proportion of interval fluctuation magnitude of the frequency spectrum is greater than a reference value, the present apparatus can objectively and accurately evaluate the degree of recovery of the subject.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
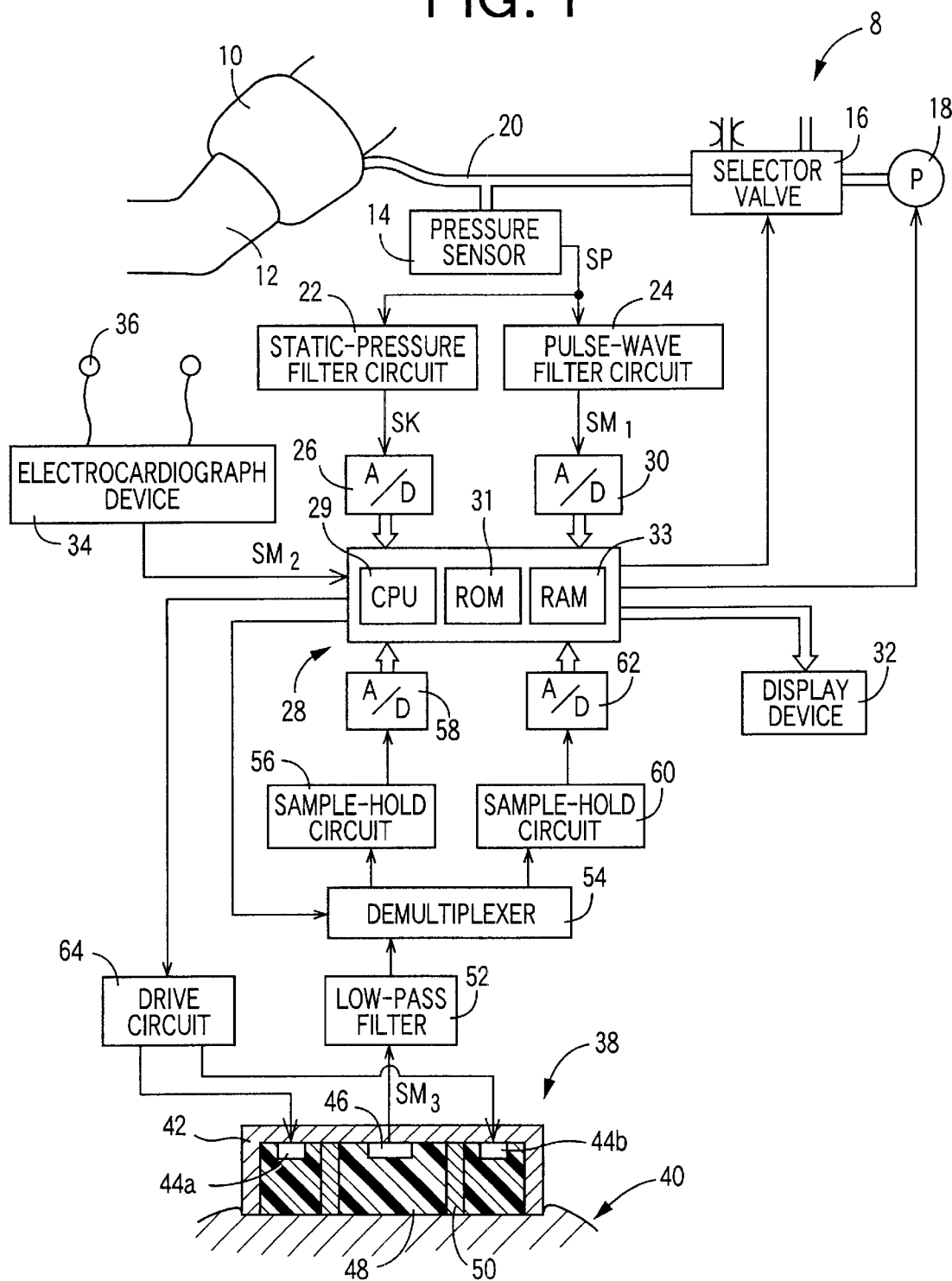
FIG. 1 is a diagrammatic view for explaining a construction of a living-subject monitoring apparatus functioning as a recovery-degree evaluating apparatus, to which the present invention is applied.

Hereinafter, there will be described an embodiment of the present invention in detail by reference to the accompanying drawings. FIG. 1 shows a diagrammatic view for explaining a construction of a living-subject monitoring apparatus 8 having the function of evaluating a postoperative condition of a living subject, to which the present invention is applied.

In FIG. 1, the living-subject monitoring apparatus 8 includes a cuff 10 which has a belt-like cloth bag and a rubber bag accommodated in the cloth bag and which is adapted to be wound around, e.g., an upper arm 12 of a patient as a living subject, and a pressure sensor 14, a selector valve 16, and an air pump 18 each of which is connected to the cuff 10 via a piping 20. The selector valve 16 is selectively placed in an inflation position in which the selector valve 16 permits a pressurized air to be supplied from the air pump 18 to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the cuff 10, and supplies a pressure signal SP representing the detected pressure, to each of a static-pressure filter circuit 22 and a pulse-wave filter circuit 24. The static-pressure filter circuit 22 includes a low-pass filter and extracts, from the pressure signal SP, a static-pressure component contained in the signal SP, i.e., a cuff-pressure signal SK representing the static pressure in the cuff 10. The cuff-pressure signal SK is supplied to an electronic control device 28 via an analog-to-digital (A/D) converter 26. The pulse-wave filter circuit 24 includes a band-pass filter and extracts, from the pressure signal SP, an oscillating component having predetermined frequencies, i.e., a pulse-wave signal $SM_1$. The pulse-wave signal $SM_1$ is supplied to the control device 28 via an A/D converter 30. The pulse-wave signal $SM_1$ represents a cuff pulse wave, i.e., a pressure wave which is produced from a brachial artery, not shown, of the patient in synchronism with the heartbeat of the patient and is propagated to the cuff 10.

The electronic control device 28 is provided by a so-called microcomputer including a central processing unit (CPU) 29, a read only memory (ROM) 31, a random access memory (RAM) 33 and an input-and-output (I/O) port, not shown. The CPU 29 processes signals according to the control programs pre-stored in the ROM 31 by utilizing the temporary-storage function of the RAM 33, and supplies drive signals to the selector valve 16 and the air pump 18 through the I/O port so as to perform a sequence of measuring actions in an oscillometric blood-pressure measuring operation and thereby measure a blood-pressure value of the patient. In addition, the CPU 29 operates a display device 32 to display the obtained blood-pressure value of the patient. The display device 32 may have a cathode ray tube (CRT).

The monitoring apparatus 8 further includes an electrocardiograph (ECG) device or ECG waveform detecting device 34 which continuously detects an electrocardiographic (ECG) waveform, i.e., an electrocardiogram (ECG) representing an action potential of cardiac muscle of the living subject, through a plurality of electrodes 36 which are adapted to be adhered to respective prescribed locations of the subject, and supplies an ECG signal $SM_2$ representing the detected ECG, to the control device 28. The control device 28 operates the display device 32 to continuously display the obtained ECG. The R-waves of the ECG are used to iteratively and accurately determine a heart rate HR of the subject, i.e., a number of heartbeats per unit time (minute).

The monitoring apparatus 8 still further includes a photoelectric-pulse-wave detecting probe 38 (hereinafter, referred to as the "probe") which is employed as part of a pulse oximeter. The probe 38 functions as a peripheral-pulse-wave detecting device for detecting a peripheral pulse wave propagated to a peripheral artery including capillaries. The probe 38 is adapted to be set on a body surface 40 of the subject, e.g., an end portion of a finger of the subject, with the help of a band, not shown, such that the probe 38 closely contacts the body surface 40. The probe 38 includes a container-like housing 42 which opens in a certain direction, a first and a second group of light emitting elements 44a, 44b, such as LEDs (light emitting diodes), which are disposed on an outer peripheral portion of an inner bottom surface of the housing 42 (hereinafter, referred to as the light emitting elements 44 in the case where the first and second group of light emitting elements 44a, 44b need not be discriminated from each other), a light receiving element 46, such as a photodiode or a phototransistor, which is disposed on a central portion of the inner bottom surface of the housing 42, a transparent resin 48 which is integrally disposed in the housing 42 to cover the light emitting elements 44 and the light receiving element 46, and an annular shade member 50 which is disposed between the light emitting elements 44 and the light receiving element 46, for preventing the lights emitted toward the body surface 40 by the light emitting elements 44 and directly reflected from the body surface 40, from being received by the light receiving element 46.

The first and second groups of light emitting elements 44a, 44b emit, e.g., a red light having about 660 nm wavelength and an infrared light having about 800 nm wavelength, respectively. The first and second light emitting elements 44a, 44b alternately emit the red and infrared lights at a predetermined frequency. The lights emitted toward the body surface 40 by the light emitting elements 44 are reflected from a body tissue of the subject where a dense capillaries occur, and the reflected lights are received by the common light receiving element 46. In place of the 660 nm and 800 nm wavelengths lights, the first and second light emitting elements 44a, 44b may emit various pairs of lights each pair of which have different wavelengths, so long as one light of the each pair exhibits significantly different absorption factors with respect to oxygenated hemoglobin and reduced hemoglobin, respectively, and the other light exhibits substantially same absorption factors with respect to the two sorts of hemoglobin, i.e., has a wavelength which is well reflected by both of the two sorts of hemoglobin.

The light receiving element 46 outputs, through a low-pass filter 52, a photoelectric-pulse-wave signal $SM_3$ representing the received or detected amount of light. The light receiving element 46 is connected to the low-pass filter 52 via an amplifier or the like. The low-pass filter 52 removes, from the photoelectric pulse-wave signal $SM_3$ input thereto, noise having frequencies higher than that of the pulse wave, and outputs the noise-free signal $SM_3$, to a demultiplexer 54. The photoelectric pulse wave represented by the photoelectric-pulse-wave signal $SM_3$ is a volumetric pulse wave which is produced in synchronism with the pulse of the patient. That is, the photoelectric pulse wave is a pulse-synchronous wave.

The demultiplexer 54 is alternately switched according to signals supplied thereto from the control device 28 in synchronism with the light emissions of the first and second light emitting elements 44a, 44b. Thus, the demultiplexer 54 successively supplies, to the I/O port, not shown, of the control device 28, an electric signal $SM_R$ representing the red light through a first sample-and-hold circuit 56 and an A/D converter 58, and an electric signal $SM_{IR}$ representing the infrared light through a second sample-and-hold circuit 60 and an A/D converter 62. The first and second sample-and-hold circuits 56, 60 hold the electric signals $SM_R$, $SM_{IR}$ input thereto, respectively, and do not output those electric signals to the A/D converters 58, 62, before the prior signals $SM_R$, $SM_{IR}$ are completely converted by the two A/D converters 58, 62, respectively.

In the control device 28, the CPU 29 generates a light emit signal SLV to a drive circuit 64 so that the first and second light emitting elements 44a, 44b alternately emit the red and infrared lights at a predetermined frequency, respectively, such that each light emission lasts for a predetermined duration. In synchronism with the alternate light emissions by the first and second light emitting elements 44a, 44b, the CPU 29 generates a switch signal SC to the demultiplexer 54 so as to correspondingly place the demultiplexer 54 in a first or a second position. Thus, the signals $SM_R$, $SM_{IR}$ are separated from each other by the demultiplexer 54 such that the signal $SM_R$ is supplied to the first sample-and-hold circuit 56 while the signal $SM_{IR}$ is supplied to the second sample-and-hold circuit 60. Further, the CPU 29 periodically determines a degree of blood oxygen saturation of the subject, based on respective amplitudes of the signals $SM_R$, $SM_{IR}$, according to a predetermined expression pre-stored in the ROM 31, and operates the display device 32 to display each of the determined degrees of blood oxygen saturation.

Figure 2:
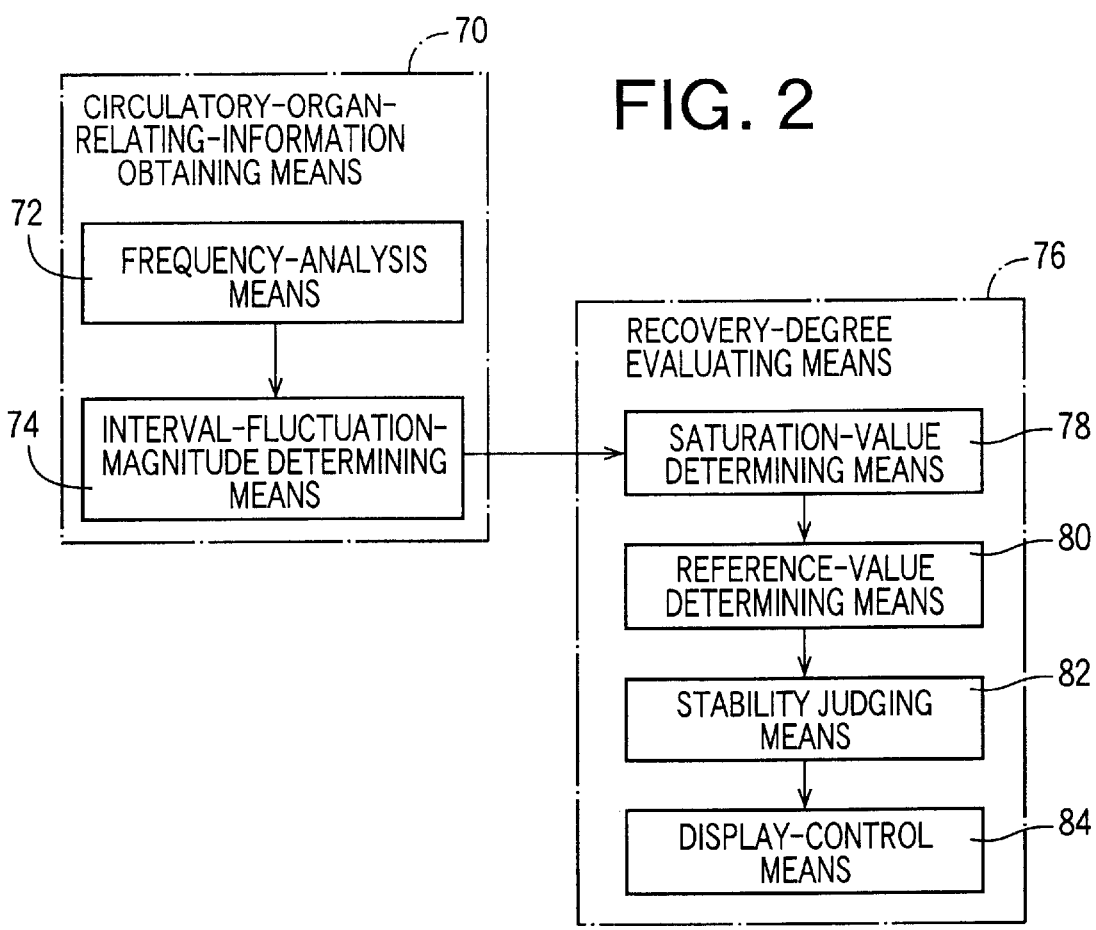
FIG. 2 is a block diagram for explaining essential functions of an electronic control device of the apparatus of FIG. 1.
Figure 3:
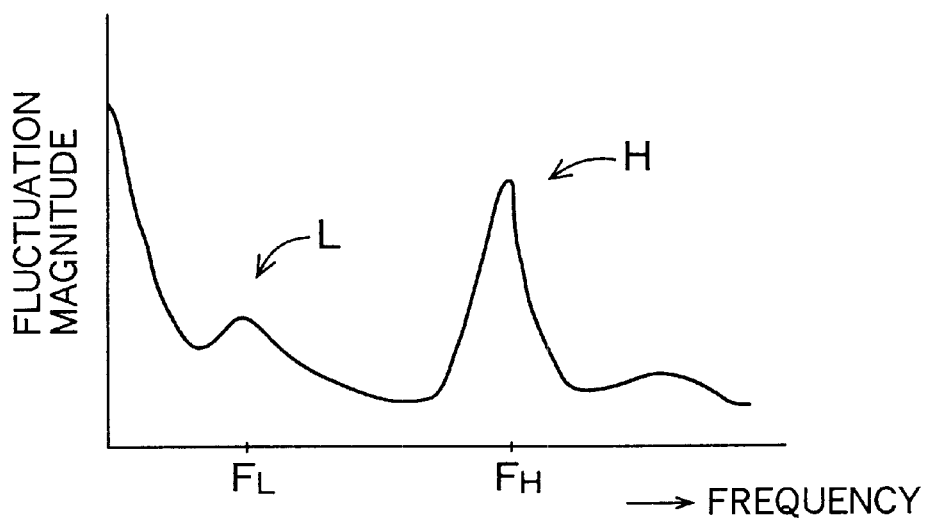
FIG. 3 is a graph showing a frequency spectrum which is obtained by a frequency-analysis means, shown in FIG. 2, from frequency analysis of heart-rate values measured from a living subject in a normal state.
Figure 4:
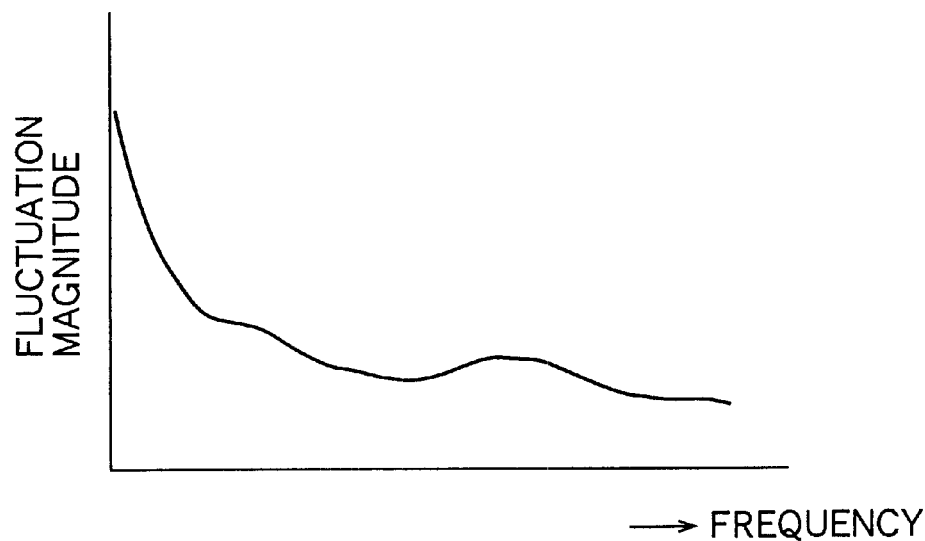
FIG. 4 is a graph showing a frequency spectrum. which is obtained by the frequency-analysis means of FIG. 2 from the frequency analysis of heart-rate values measured from a living subject during a surgical operation or immediately after the same.

FIG. 2 is a block diagram for explaining essential functions of the electronic control device 28 of the living-subject monitoring apparatus 8, for evaluating a degree of recovery of a living subject from a surgical operation. In the figure, a circulatory-organ-relating-information obtaining means 70 iteratively obtains, as a sort of information relating to the circulatory organ of the living subject, a fluctuation-magnitude signal representing a magnitude of a fluctuation of the heart rate HR whose values are iteratively determined based the ECG signal $SM_2$ supplied from the ECG device 34. To this end, the information obtaining means 70 includes a frequency-analysis means 72 and an interval-fluctuation-magnitude determining means 74. The frequency-analysis means 72 subjects the heart-rate values HR iteratively determined based on successive heartbeat-synchronous pulses of the ECG signal $SM_2$, to a frequency analysis, e.g., FFT (fast Fourier transform). If the heart rate values HR of the living subject are finely observed, then it can be found that the heart rate values HR have small fluctuations. FIGS. 3 and 4 show results which are obtained by subjecting heart rate values HR to the frequency analysis. FIG. 3 shows a frequency distribution or spectrum which is obtained from a living subject who is in a normal or resting state. The frequency spectrum of FIG. 3 has a clear low-frequency peak L and a clear high-frequency peak H both of which relate to a degree of activity of the autonomic nerve system of the living subject. FIG. 4 shows a frequency spectrum which is obtained, e.g., immediately after a surgical operation, from a living subject whose autonomic nerve system is paralyzed or embarrassed by, e.g., anesthesia or surgical injury. The frequency spectrum of FIG. 4 does not have a clear low-frequency peak L or a clear high-frequency peak H. As time passes after the surgical operation, that is, as the degree of recovery of the living subject increases and accordingly the postoperative condition of the subject becomes more stable, the high-frequency peak H or the low-frequency peak L changes from a first state indicated at solid line in FIG. 5 (only the three states of peak H are shown), to a second state indicated at one-dot chain line, and then to a third state indicated at two-dot chain line, that is, a fluctuation-magnitude signal (unit: power) increases, simultaneously a degree of sharpness of each peak H, L corresponding to a fluctuation frequency increases, and a central frequency $F_H$, $F_L$ of each peak H, L changes from a first value (e.g., $F_{H1}$ shown in FIG. 5), to a second value (e.g., $F_{H2}$), and then to a third value (e.g., $F_{H3}$). Since a rate of change of each circulatory-organ-relating information gradually decreases as time passes, a time-wise change of each sort of circulatory-organ-relating information can be expressed by a logarithmic function. It is known in the art that the low-frequency peak L occurs to a frequency interval from 0.04 to 0.15 Hz and the high-frequency peak H occurs to a frequency interval from 0.15 to 0.4 Hz.

Figure 17:
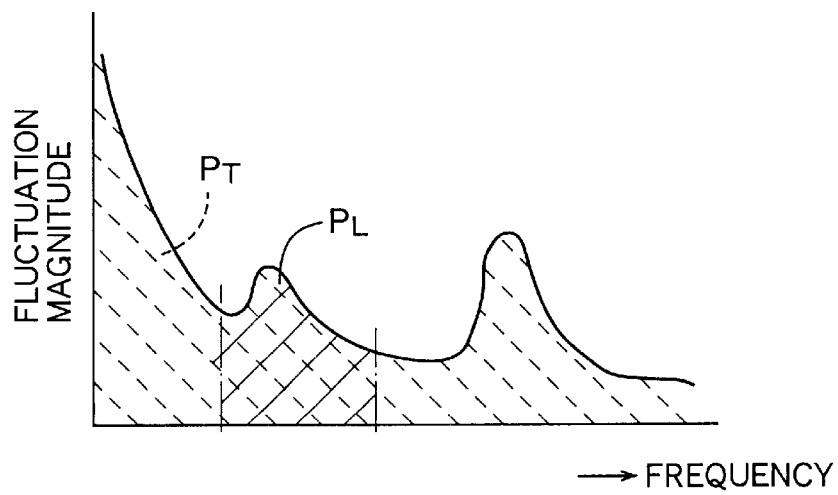
FIG. 17 is a graph for explaining an interval-fluctuation-magnitude proportion which is determined by an interval-fluctuation-magnitude-proportion determining means, shown in FIG. 16.

The interval-fluctuation-magnitude determining means 74 determines, based on a frequency spectrum obtained by the frequency-analysis means 72, a low-frequency fluctuation magnitude $P_L$ of a low-frequency peak L, i.e., an area enveloped by a portion of the fluctuation-magnitude signal (i.e., the frequency spectrum) in a prescribed low-frequency interval of from 0.04 to 0.15 Hz, as shown in FIG. 17, and a high-frequency fluctuation magnitude $P_H$ of a high-frequency peak H, i.e., an area enveloped by a portion of the fluctuation-magnitude signal in a prescribed high-frequency interval of from 0.15 to 0.4 Hz.

A recovery-degree evaluating means 76 evaluates, based on a time-wise change of the fluctuation magnitudes $P_L$, $P_H$ of the heart rate HR that are iteratively obtained by the circulatory-organ-relating-information obtaining means 70, a degree of recovery of a living subject from a surgical operation, i.e., a postoperative condition of the same. To this end, the evaluating means 76 includes a saturation-value determining means 78, a reference-value determining means 80, a stability judging means 82, and a display-control means 84. The saturation-value determining means 78 determines, based on the low-frequency and/or high-frequency fluctuation magnitudes $P_L$, $P_H$ of the heart rate HR, a low-frequency saturation value $P_{LE}$, and/or a high-frequency saturation value $P_{HE}$, using the following logarithmic functions (1), (2) representing a time-wise change of the low-frequency or high-frequency fluctuation magnitudes $P_L$, $P_H$:

$$P_L(t)=P_{LE}(1-e^{-t/RC}) \quad (1)$$

$$P_H(t)=P_{HE}(1-e^{-t/RC}) \quad (2)$$

For example, in the case where the high-frequency saturation value $P_{HE}$ is determined, at least two simultaneous equations are obtained, according to the logarithmic function (2), from at least two high-frequency fluctuation magnitudes $P_H$ and respective times when those magnitudes $P_H$ are iteratively obtained. If the simultaneous equations are solved by eliminating a time constant RC as one of two unknowns RC, $P_{HE}$ of the function (2), then the saturation value $P_{HE}$ as the other unknown is determined.

Figure 6:
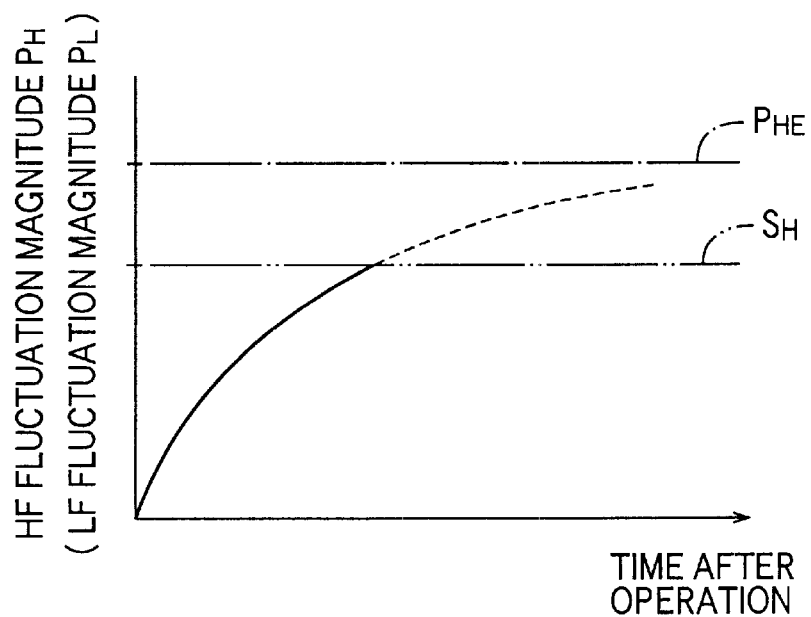
FIG. 6 is a view for explaining a screen image which is displayed by a display device of the apparatus of FIG. 1 when a stability judging means, shown in FIG. 2, judges that a degree of recovery of a living subject from a surgical operation has entered a stable range.

The reference-value determining means 80 determines, based on the low-frequency and/or high-frequency saturation value $P_{LE}$, $P_{HE}$ determined by the saturation-value determining means 78, a low-frequency and/or a high-frequency reference value $S_L$, $S_H$ which are smaller than the low-frequency and/or high-frequency saturation value $P_{LE}$, $P_{HE}$, respectively. Each reference value S ($S_L$, $S_H$) is used in judging whether the living subject has recovered from the surgical operation. For example, the determining means 80 determines the low-frequency and high-frequency reference values $S_L$, $S_H$ by multiplying the low-frequency and high-frequency saturation values $P_{LE}$, $P_{HE}$, each by 0.7 that is an empirically obtained coefficient. The stability judging means 82 judges whether each of the actual low-frequency or high-frequency fluctuation magnitudes $P_L$, $P_H$ is greater than the low-frequency or high-frequency reference values $S_L$, $S_H$, and if a positive judgment is made, judges that the degree of recovery of the living subject from the surgical operation has entered a stable range (i.e., a stable state). The display-control means 84 operates the display device 32 to display a graph showing, in a two-dimensional coordinate system having a time axis and a fluctuation magnitude axis, the low-frequency and/or high-frequency saturation value $P_{HE}$, $P_{LE}$, the low-frequency ("LF") and/or high-frequency ("HF") reference value $S_L$, $S_H$, and each of the actual low-frequency and/or high-frequency fluctuation magnitudes $P_L$, $P_H$, as shown in FIG. 6 (only the high-frequency saturation and reference values $P_{HE}$, $S_H$ are shown in FIG. 6). In addition, the display-control means 84 operates the display device 32 to display a message or a color, or light a lamp, indicating the positive or negative judgment made by the stability judging means 82.

Figure 7:
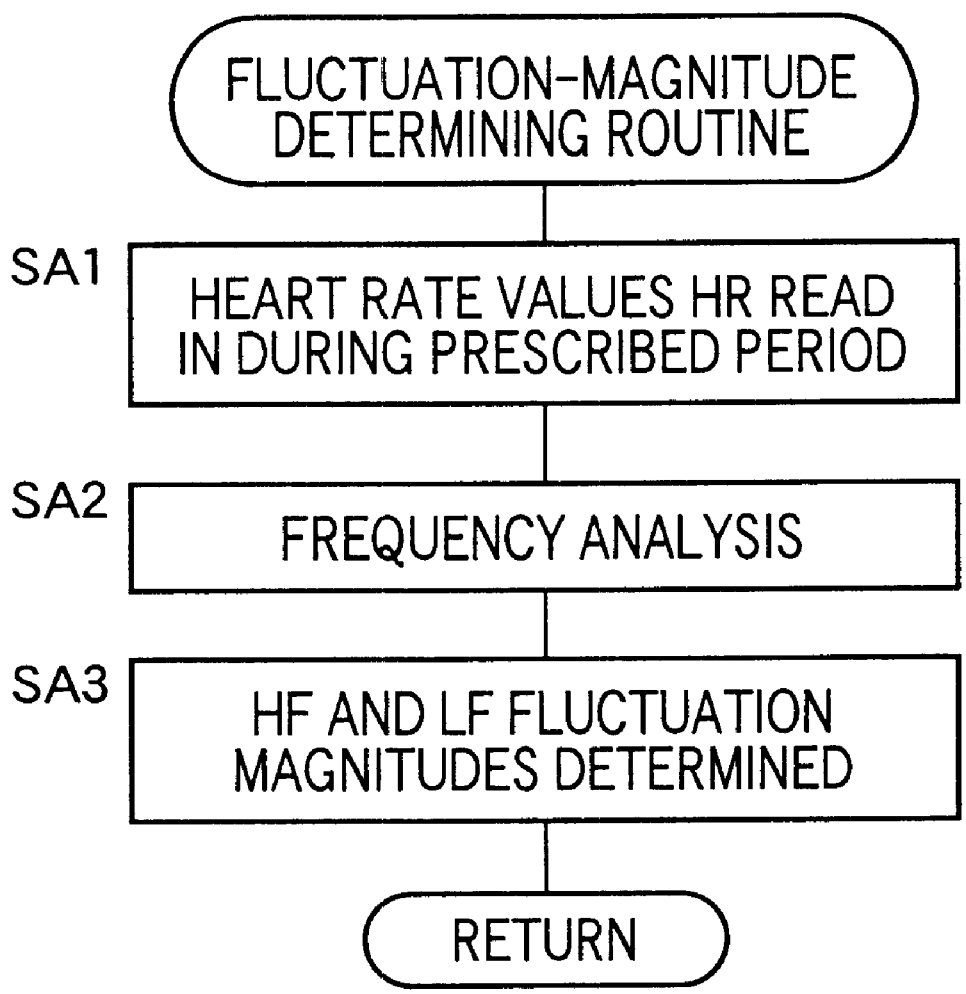
FIG. 7 is a flow chart representing a fluctuation-magnitude determining routine according to which the control device of FIG. 2 determines a magnitude of a fluctuation of heart-rate values measured from a living subject.
Figure 8:
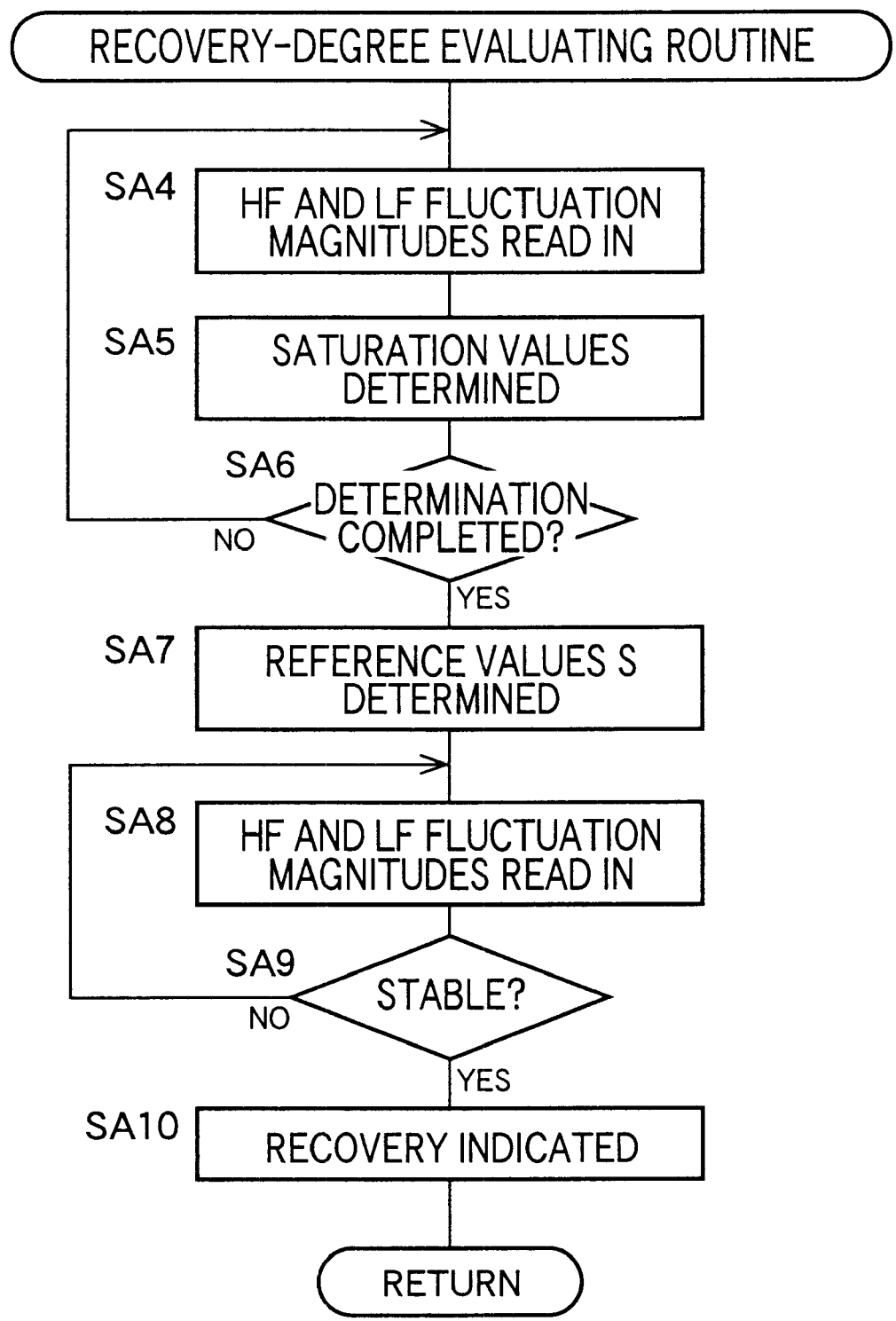
FIG. 8 is a flow chart representing a recovery-degree evaluating routine according to which the control device of FIG. 2 evaluates a degree of recovery of a living subject.

Next, there will be described a recovery-degree evaluating operation of the electronic control device 28 of the living-subject monitoring apparatus 8, by reference to the flow charts of FIGS. 7 and 8. FIG. 7 shows a fluctuation-magnitude determining routine, and FIG. 8 shows a recovery-degree evaluating routine. At Step SA1 (hereinafter, "Step" is omitted) of FIG. 7, the control device 28 iteratively determines a heart rate value HR based on each of heartbeat-synchronous pulses of the ECG signal $SM_2$ supplied from the ECG device 24, and reads in the heart rate values HR determined in a prescribed time period. This time period is so prescribed that the control device 28 can read in a sufficient number of heart rate values HR for carrying out a frequency analysis of the same. In the present embodiment, the time period is so prescribed as to be able to read in at least six heart rate values HR. Next, at SA2 corresponding to the frequency-analysis means 72, the control device 28 carries out a frequency analysis on the heart rate values HR read in at SA1. Then, at SA3 corresponding to the interval-fluctuation-magnitude determining means 74, the control device 28 determines, based on a frequency spectrum obtained at SA2, a low-frequency fluctuation magnitude $P_L$ of a low-frequency peak L in a prescribed low-frequency interval from 0.04 to 0.15 Hz, and a high-frequency fluctuation magnitude $P_H$ of a high-frequency peak H in a prescribed high-frequency interval from 0.15 to 0.4 Hz. The routine of FIG. 7 corresponds to the circulatory-organ-relating-information obtaining means 70, and the control device 28 executes this routine at a prescribed period. Thus, the control device 28 iteratively determines the low-frequency fluctuation magnitude $P_L$ and the high-frequency fluctuation magnitude $P_H$ of the living subject.

At SA4 of FIG. 8, the control device 28 reads in the low-frequency fluctuation magnitude $P_L$ and the high-frequency fluctuation magnitude $P_H$ of the living subject, determined at SA3. Next, at SA5 corresponding to the saturation-value determining means 78, the control device 28 determines, based on the low-frequency fluctuation magnitude $P_L$ and the high-frequency fluctuation magnitude $P_H$, a low-frequency saturation value $P_{LE}$ and a high-frequency saturation value $P_{HE}$, using the functions (1), (2) representing respective time-wise changes of low-frequency fluctuation magnitudes $P_L$ and high-frequency fluctuation magnitudes $P_H$. Then, at SA6, the control device 28 judges whether the low-frequency saturation value $P_{LE}$ and the high-frequency saturation value $P_{HE}$, have been determined at SA5. Each saturation value $P_{LE}$, $P_{HE}$, cannot be determined without solving at least two simultaneous equations. Accordingly, in the first control cycle according to the routine of FIG. 8, a negative judgment is made at SA6, and the control device 28 repeats SA4 and the following steps. Meanwhile, if a positive judgment is made at SA6, the control of the control device 28 proceeds with SA7 corresponding to the reference-value determining means 80, where the control device 28 determines, based on the low-frequency and high-frequency saturation values PLE, $P_{HE}$ determined at SA5, a low-frequency reference value $S_L$ and a high-frequency reference value $S_H$ which are smaller than the low-frequency and high-frequency saturation values $P_{LE}$, $P_{HE}$, respectively, by multiplying the saturation values $P_{LE}$, $P_{HE}$, each by a prescribed coefficient, e.g., 0.7.

Next, at SA8, the control device 28 reads in the low-frequency fluctuation magnitude $P_L$ and the high-frequency fluctuation magnitude $P_H$ of the living subject, determined at SA3. Then, at Step SA9 corresponding to the stability judging means 82, the control device 28 judges whether the low-frequency fluctuation magnitude $P_L$ is greater than the low-frequency reference value $S_L$, and/or whether the high-frequency fluctuation magnitude $P_H$ is greater than the high-frequency reference value $S_H$. If the fluctuation magnitude $P_L$ is greater than the reference value $S_L$, or if the fluctuation magnitude $P_H$ is greater than the reference value $S_H$, the control device 28 judges that the degree of recovery of the living subject from the surgical operation has entered a stable range (i.e., a stable state). Then, at SA10 corresponding to the display-control means 84, the control device 28 operates the display device 32 to display a graph showing, in a two-dimensional coordinate system having a time axis and a fluctuation-magnitude axis, the low-frequency or high-frequency saturation value $P_{HE}$, $P_{LE}$, the low-frequency ("LF") or high-frequency ("HF") reference value $S_L$, $S_H$, and each of the actual low-frequency or high-frequency fluctuation magnitudes $P_L$, $P_H$, as shown in FIG. 6. In addition, the control device 28 operates the display device 32 to display a message or a color, or light a lamp, indicating the positive or negative judgment made at SA9.

It emerges from the foregoing description of the present embodiment that the circulatory-organ-relating-information obtaining means 70 (SA1 to SA3) iteratively obtains, from a living subject who has undergone a surgical operation, pieces of circulatory-organ-relating information, i.e., low-frequency fluctuation magnitudes $P_L$ corresponding to the low-frequency peak L, or high-frequency fluctuation magnitudes $P_H$ corresponding to the high-frequency peak H; and the recovery-degree evaluating means 76 (SA1 to SA10) evaluates a degree of recovery of the living subject from the surgical operation, based on a change of the pieces of circulatory-organ-relating information. Thus, the present apparatus 8 can objectively and accurately evaluate the degree of recovery of the subject.

In addition, in the present embodiment, the recovery-degree evaluating means 76 (SA1 to SA10) evaluates the degree of recovery of the subject from the operation, by judging whether the rate of change of the pieces of circulatory-organ-relating information, i.e., the fluctuation magnitudes $P_L$ corresponding to the peak L, or the fluctuation magnitudes $P_H$ corresponding to the peak H has decreased and become stable. The pieces of circulatory-organ-relating information iteratively obtained by the circulatory-organ-relating-information obtaining means 70 from the subject after the operation will change toward a saturation value and will be stable around the same value. Since the present apparatus 8 evaluates the degree of recovery of the subject by judging whether the change of the pieces of circulatory-organ-relating information has decreased to not greater than a certain amount and has become stable, it can objectively and accurately evaluate the degree of recovery of the subject.

In addition, in the present embodiment, the recovery-degree evaluating means 76 (SA1 to SA10) determines, based on the time-wise change of the pieces of circulatory-organ-relating information, i.e., the fluctuation magnitudes $P_L$ corresponding to the peak L, or the fluctuation magnitudes $P_H$ corresponding to the peak H, a saturation value $P_{LE}$, $P_{HE}$ for the pieces of circulatory-organ-relating information, determines a reference value $S_L$, $S_H$ which is smaller than the saturation value $P_{LE}$, $P_{HE}$, and evaluates the degree of recovery of the subject by judging whether each of the actual fluctuation magnitudes $P_L$ corresponding to the peak L is greater than the reference value $S_L$, or whether each of the actual fluctuation magnitudes $P_H$ corresponding to the peak H is greater than the reference value $S_H$. Since the pieces of circulatory-organ-relating information iteratively obtained from the subject after the operation change substantially faithfully along a logarithmic curve, the change of the information can be represented by a logarithmic function. Thus, the present apparatus 8 can determine, based on a time-wise change of the fluctuation magnitudes $P_L$ corresponding to the peak L, or the fluctuation magnitudes $P_H$ corresponding to the peak H, a saturation value $P_{LE}$ or a saturation value $P_{HE}$ for each of individual living subjects. Therefore, the present apparatus 8 can accurately evaluate the degree of recovery of each living subject, irrespective of individual differences, by judging whether each of the fluctuation magnitudes $P_L$ corresponding to the peak L is greater than a reference value $S_L$ smaller than the saturation value $P_{LE}$, or whether each of the fluctuation magnitudes $P_H$ corresponding to the peak H is greater than a reference value $S_H$ smaller than the saturation value $P_{HE}$.

Next, there will be described a second embodiment of the present invention that also relates to a living-subject monitoring apparatus having the same hardware construction as that of the monitoring apparatus 8, shown in FIG. 1, as the first embodiment. In the following description, the same reference numerals as used in the first embodiment are used to designate the corresponding elements of the second embodiment, and the description thereof is omitted.

Figure 9:
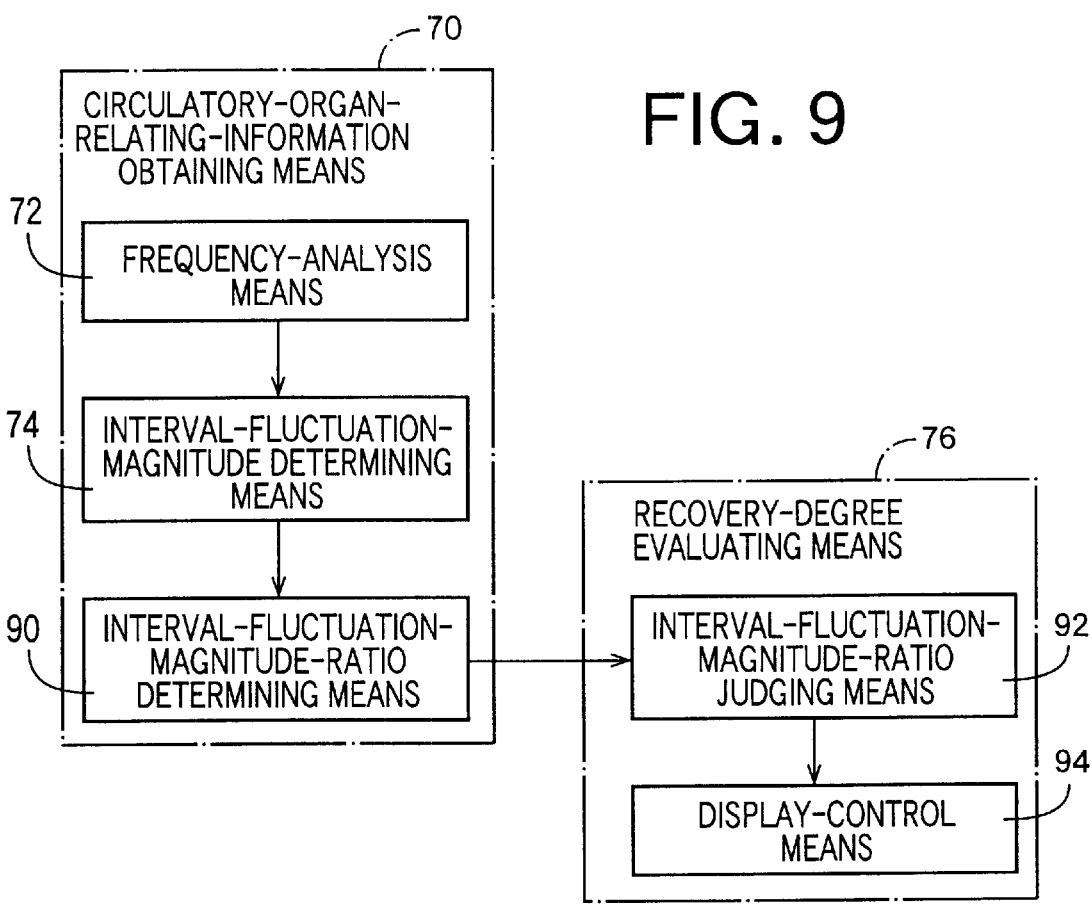
FIG. 9 is a block diagram corresponding to FIG. 2, for explaining essential functions of an electronic control device of another living-subject monitoring apparatus as a second embodiment of the present invention.

FIG. 9 is a block diagram for explaining essential functions of the electronic control device 28 of the present living-subject monitoring apparatus as the second embodiment, including a recovery-degree evaluating function. In the figure, a circulatory-organ-relating-information obtaining means 70 iteratively obtains, as a sort of information relating to circulatory organ of a living subject, an interval-fluctuation-magnitude ratio $P_L/P_H$, that is, a ratio of (a) a low-frequency fluctuation magnitude $P_L$ of the heart rate values HR determined based the ECG signal $SM_2$ supplied from the ECG device 34, to (b) a high-frequency fluctuation magnitude $P_H$ of the heart rate values HR. To this end, the information obtaining means 70 includes a frequency-analysis means 72, an interval-fluctuation-magnitude determining means 74, and an interval-fluctuation-magnitude-ratio determining means 90. The interval-fluctuation-magnitude determining means 74 iteratively determines, based on a frequency spectrum, shown in FIG. 3 or 4, obtained from the heart rate values HR, a low-frequency fluctuation magnitude $P_L$ of a low-frequency peak L in a prescribed low-frequency interval, and a high-frequency fluctuation magnitude $P_H$ of a high-frequency peak H in a prescribed high-frequency interval. The interval-fluctuation-magnitude-ratio determining means 90 iteratively determines an interval-fluctuation-magnitude ratio $P_L/P_H$, that is, a ratio of (a) a low-frequency fluctuation magnitude $P_L$ to (b) a high-frequency fluctuation magnitude $P_H$.

A recovery-degree evaluating means 76 evaluates, based on each of the interval-fluctuation-magnitude ratios $P_L/P_H$ iteratively determined by the circulatory-organ-relating-information obtaining means 70, a degree of recovery of a living subject from a surgical operation. To this end, the evaluating means 76 includes an interval-fluctuation-magnitude judging means 92, and a display-control means 94. The interval-fluctuation-magnitude judging means 92 judges whether each of the interval-fluctuation-magnitude ratios $P_L/P_H$ is greater than a prescribed reference value $R_1$ and, if a positive judgment is made, judges that the living subject has recovered from the surgical operation. It is speculated that the interval-fluctuation magnitude ratio $P_L/P_H$ obtained from the heart rate values HR is an amount which closely reflects the activity of the sympathetic nerve system of the subject. Thus, the present monitoring apparatus evaluates the degree of recovery of the living subject from the operation, by judging whether the activity of the sympathetic nerve system of the subject has become stable. The display-control means 94 operates the display device 32 to display a message or a color, or light a lamp, indicating the positive or negative judgment made by the interval-fluctuation-magnitude judging means 92.

Figure 10:
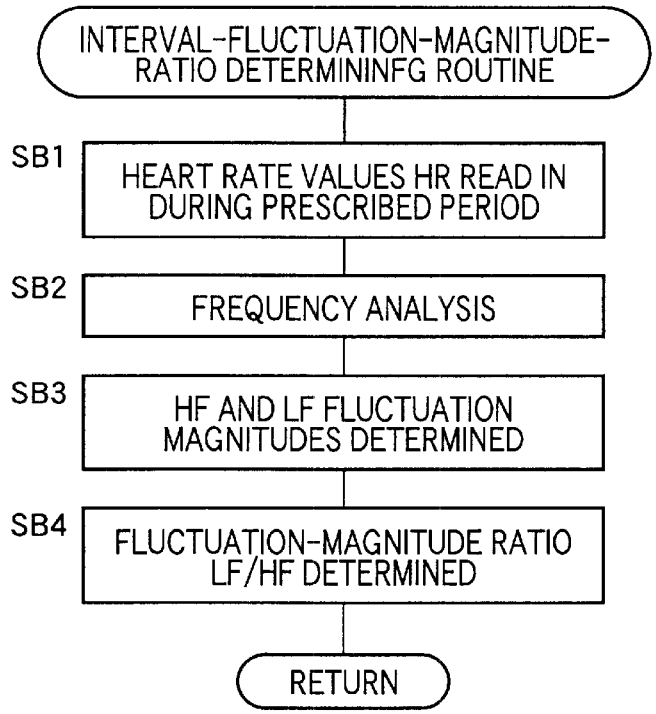
FIG. 10 is a flow chart representing a fluctuation-magnitude-ratio determining routine according to which the control device of FIG. 9 determines a fluctuation-magnitude ratio.
Figure 11:
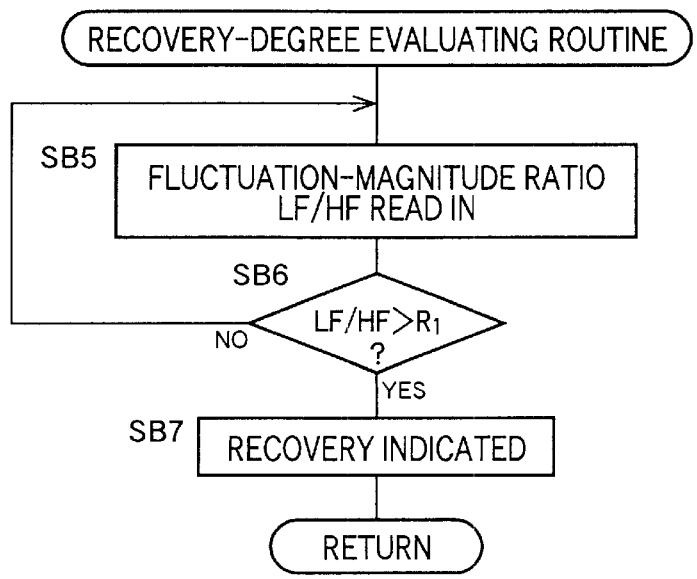
FIG. 11 is a flow chart representing a recovery-degree evaluating routine according to which the control device of FIG. 9 evaluates a degree of recovery of a living subject.

Next, there will be described a recovery-degree evaluating operation of the electronic control device 28 of the second monitoring apparatus, by reference to the flow charts of FIGS. 10 and 11. FIG. 10 shows an interval-fluctuation-magnitude-ratio determining routine, and FIG. 11 shows a recovery-degree evaluating routine. At Step SB1 (hereinafter, "Step" is omitted), SB2 corresponding to the frequency-analysis means 72, and SB3 corresponding to the interval-fluctuation-magnitude determining means 74, the control device 28 operates like at SA1, SA2, and SA3 of FIG. 7, that is, reads in the heart rate values HR, subjects the heart rate values HR to the frequency analysis, and iteratively determines, based on the obtained frequency spectrum, a low-frequency fluctuation magnitude $P_L$ corresponding to a flow-frequency peak L in a prescribed low-frequency interval, and a high-frequency fluctuation magnitude $P_H$ corresponding to a flow-frequency peak H in a prescribed high-frequency interval. Then, at SB4 corresponding to the interval-fluctuation-magnitude-ratio determining means 90, the control device 28 iteratively determines a ratio $P_L/P_H$ of the low-frequency fluctuation magnitude $P_L$, determined at SB3, to the high-frequency fluctuation magnitude $P_H$, determined at SB3.

At SB5 of FIG. 11, the control device 28 reads in the interval-fluctuation-magnitude ratio $P_L/P_H$ determined at SB4. Next, at SB6 corresponding to the interval-fluctuation-magnitude-ratio judging means 92, the control device 28 judges whether the interval-fluctuation-magnitude ratio $P_L/P_H$ read in at SB5 is greater than a prescribed reference value $R_1$. The reference value $R_1$ is experimentally obtained as a value indicating that the activity of the sympathetic nerve system of the living subject after the surgical operation has increased to not smaller than a certain value and accordingly the subject has recovered from the operation. If a negative judgment is made at SB6, the control device 28 repeats SB5 and SB6. Meanwhile, if a positive judgment is made at SB6, the control goes to SB7 corresponding to the display-control means 94, where the control device 28 operates the display device 32 to indicate that the subject has recovered from the operation.

It is speculated that the interval-fluctuation-magnitude ratio $P_L/P_H$ as the ratio of one of the low-frequency fluctuation-magnitude $P_L$ and the high-frequency fluctuation-magnitude $P_H$ of the heart rate values HR of the living subject to the other of the fluctuation magnitudes $P_L$, $P_H$ faithfully reflects the activity of the sympathetic nerve system of the subject. The present monitoring apparatus evaluates the degree of recovery of the subject, by judging whether the interval-fluctuation magnitude ratio $P_L/P_H$ is greater than the prescribed reference value $R_1$. Thus, the present monitoring apparatus can objectively and accurately evaluate the degree of recovery of the subject.

Next, there will be described a third embodiment of the present invention that also relates to a living-subject monitoring apparatus having the same hardware construction as that of the monitoring apparatus 8, shown in FIG. 1, as the first embodiment. In the following description, the same reference numerals as used in the first embodiment are used to designate the corresponding elements of the third embodiment, and the description thereof is omitted.

Figure 12:
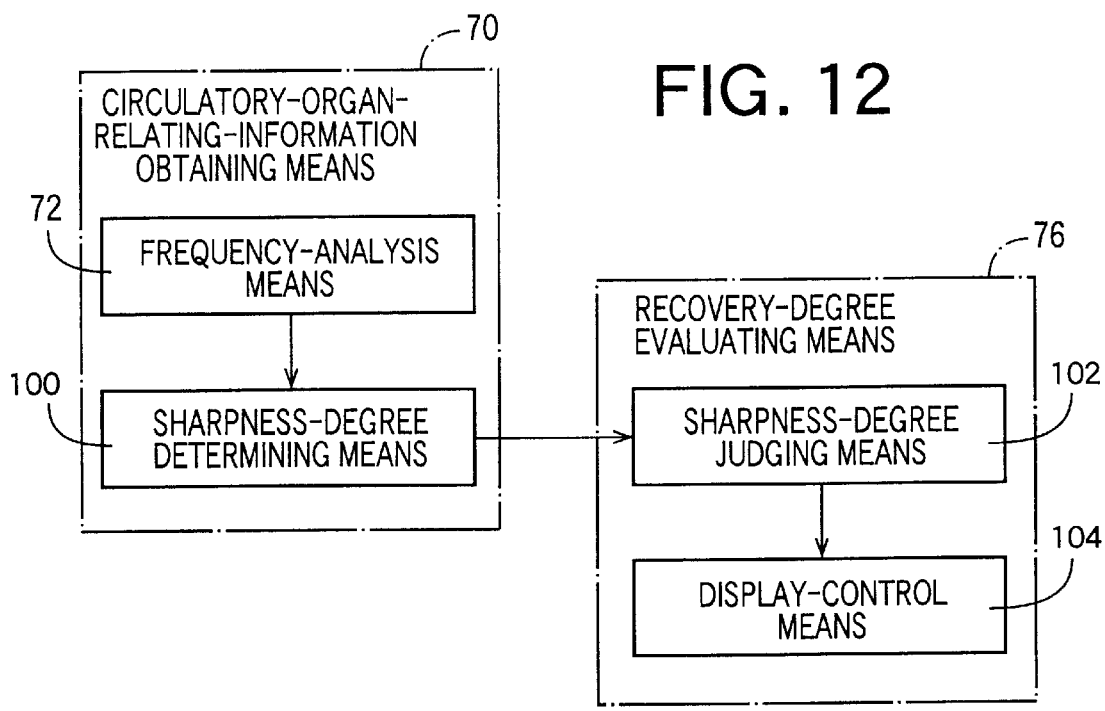
FIG. 12 is a block diagram corresponding to FIG. 2, for explaining essential functions of an electronic control device of another living-subject monitoring apparatus as a third embodiment of the present invention.
Figure 13:
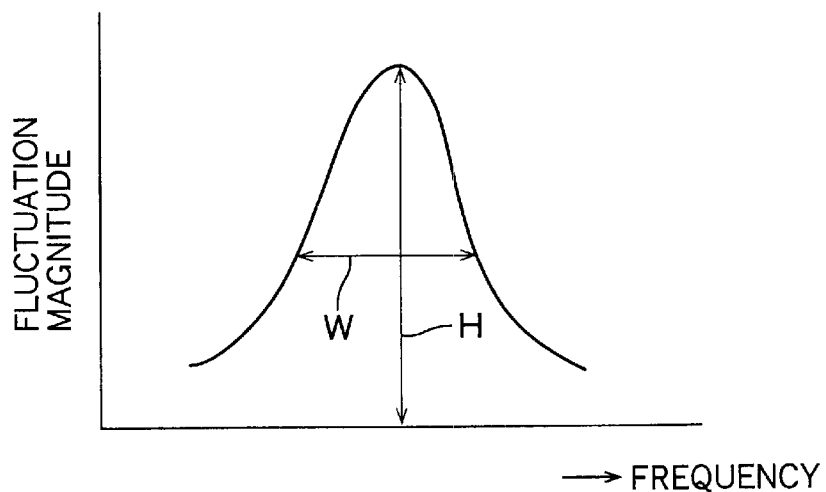
FIG. 13 is a graph for explaining a degree of sharpness which is determined by a sharpness-degree determining means, shown in FIG. 12.

FIG. 12 is a block diagram for explaining essential functions of the electronic control device 28 of the present living-subject monitoring apparatus as the third embodiment, including a recovery-degree evaluating function. In the figure, a circulatory-organ-relating-information obtaining means 70 iteratively obtains, as a sort of information relating to circulatory organ of a living subject, a degree of sharpness $K_L$ of a low-frequency peak L of a frequency spectrum obtained from the heart rate values HR determined based the ECG signal $SM_2$ supplied from the ECG device 34, and/or a degree of sharpness $K_H$ of a high-frequency peak H of the frequency spectrum. To this end, the information obtaining means 70 includes a frequency-analysis means 72, and a sharpness-degree determining means 100. The sharpness-degree determining means 100 iteratively determines, based on a frequency spectrum, shown in FIG. 3 or 4, obtained by the frequency analysis of the frequency-analysis means 72 from the heart rate values HR, a degree of sharpness $K_L$ of a waveform of a low-frequency peak L occurring to a prescribed low-frequency interval, and/or a degree of sharpness $K_H$ of a waveform of a high-frequency peak H occurring to a prescribed high-frequency interval. In the present embodiment, the sharpness degree $K_L$, $K_H$ is defined, as illustrated in FIG. 13, as a ratio H/W of a height H of a waveform of a peak L, H to a width W of the peak L, H at half the height H. However, the sharpness degree $K_L$, $K_H$ may be defined in a different manner.

Figure 5:
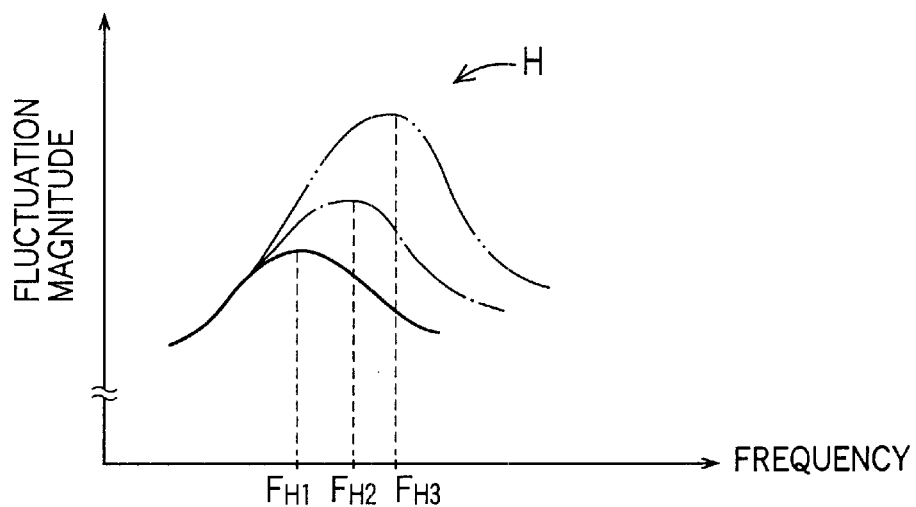
FIG. 5 is a graph showing a time-wise change of a waveform of a peak occurring to the frequency spectrum of FIG. 3.

A recovery-degree evaluating means 76 evaluates, based on each of the low-frequency and/or high-frequency sharpness degrees $K_L$, $K_H$ iteratively determined by the circulatory-organ-relating-information obtaining means 70, a degree of recovery of a living subject from a surgical operation. To this end, the evaluating means 76 includes a sharpness-degree judging means 102 and a display-control means 104. The sharpness-degree judging means 102 judges whether each of the low-frequency sharpness-degree values $K_L$ is greater than a prescribed reference value $K_{L1}$ and/or whether each of the high-frequency sharpness-degree values $K_H$ is greater than a prescribed reference value $K_{H1}$. And, if a positive judgment is made, the judging means 102 judges that the living subject has recovered from the surgical operation. It is speculated that the sharpness degree $K_L$, $K_H$ obtained from the heart rate values HR is, as illustrated in FIG. 5, an amount which closely reflects the degree of recovery of the autonomic nerve system of the subject. Thus, the present monitoring apparatus evaluates the degree of recovery of the living subject from the operation, by judging whether the activity of the autonomic nerve system of the subject has become stable. The display-control means 104 operates the display device 32 to display a message or a color, or light a lamp, indicating the positive or negative judgment made by the sharpness-degree judging means 102.

Figure 14:
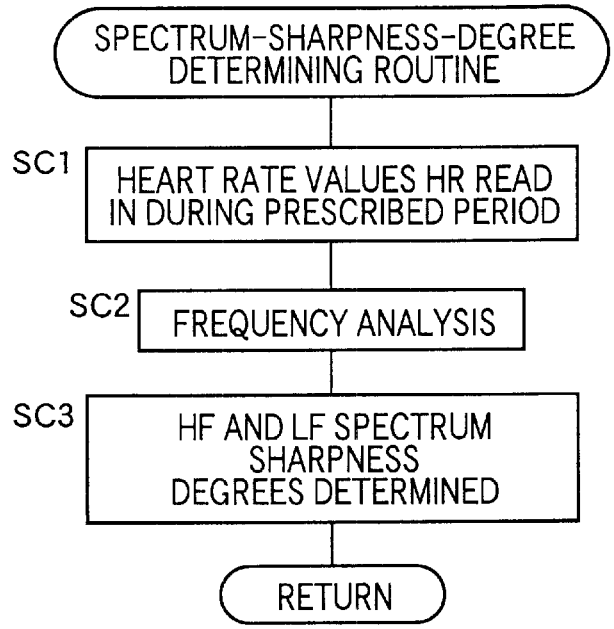
FIG. 14 is a flow chart representing a sharpness-degree determining routine according to which the control device of FIG. 12 determines a degree of sharpness.
Figure 15:
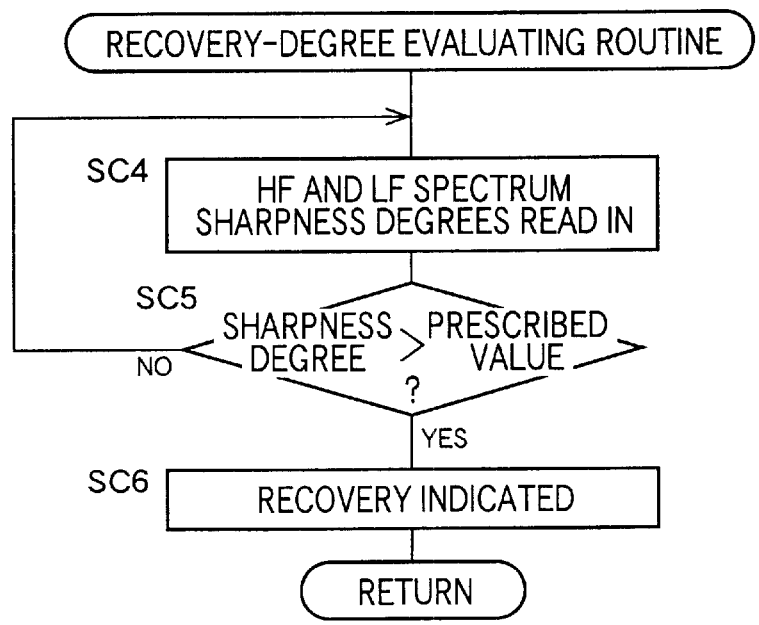
FIG. 15 is a flow chart representing a recovery-degree evaluating routine according to which the control device of FIG. 12 evaluates a degree of recovery of a living subject.

Next, there will be described, a recovery-degree evaluating operation of the electronic control device 28 of the third monitoring apparatus, by reference to the flow charts of FIGS. 14 and 15. FIG. 14 shows a sharpness-degree determining routine, and FIG. 15 shows a recovery-degree evaluating routine. At Step SC1 (hereinafter, "Step" is omitted), and SC2 corresponding to the frequency-analysis means 72, the control device 28 operates like at SA1 and SA2 of FIG. 7, that is, reads in the heart rate values HR, and subjects the heart rate values HR to the frequency analysis. Then, at SC3 corresponding to the sharpness-degree determining means 100, the control device 28 iteratively determines, based on the frequency spectrum obtained at SC2, a degree of sharpness $K_L$ of a waveform of a low-frequency peak L of the frequency spectrum and/or a degree of sharpness $K_H$ of a waveform of a high-frequency peak H of the same frequency spectrum.

Next, at SC4 of FIG. 15, the control device 28 reads in the low-frequency-peak sharpness degree $K_L$ and/or the high-frequency-peak sharpness degree $K_H$ determined at SC3. Then, at SC5 corresponding to the sharpness-degree judging means 102, the control device 28 judges whether the low-frequency-peak sharpness degree $K_L$ is greater than a prescribed reference value $K_{L1}$, and/or whether the high-frequency-peak sharpness degree $K_H$ is greater than a prescribed reference value $K_{H1}$. Each of the reference values $K_{L1}$, $K_{H1}$ is experimentally obtained as a value indicating that the activity of the autonomic nerve system of the living subject after the surgical operation has increased to not smaller than a certain value and accordingly the subject has recovered from the operation. If a negative judgment is made at SC5, the control device 28 repeats SC4 and SC5. Meanwhile, if a positive judgment is made at SC5, the control goes to SC6 corresponding to the display-control means 104, where the control device 28 operates the display device 32 to indicate that the subject has recovered from the operation.

It is speculated that the sharpness degree $K_L$ of waveform of the low-frequency peak L, and/or the sharpness degree $K_H$ of waveform of the high-frequency peak H, of the frequency spectrum of the heart rate values HR of the living subject reflects the activity of the sympathetic and parasympathetic nerve systems of the subject. The present monitoring apparatus evaluates the degree of recovery of the subject, by judging whether the low-frequency-peak sharpness degree $K_L$ is greater than the prescribed reference value $K_{L1}$, and/or judging whether the high-frequency-peak sharpness degree $K_H$ is greater than the prescribed reference value $K_{H1}$. Thus, the present monitoring apparatus can objectively and accurately evaluate the degree of recovery of the subject.

Next, there will be described a fourth embodiment of the present invention that also relates to a living-subject monitoring apparatus having the same hardware construction as that of the monitoring apparatus 8, shown in FIG. 1, as the first embodiment. In the following description, the same reference numerals as used in the first embodiment are used to designate the corresponding elements of the fourth embodiment, and the description thereof is omitted.

Figure 16:
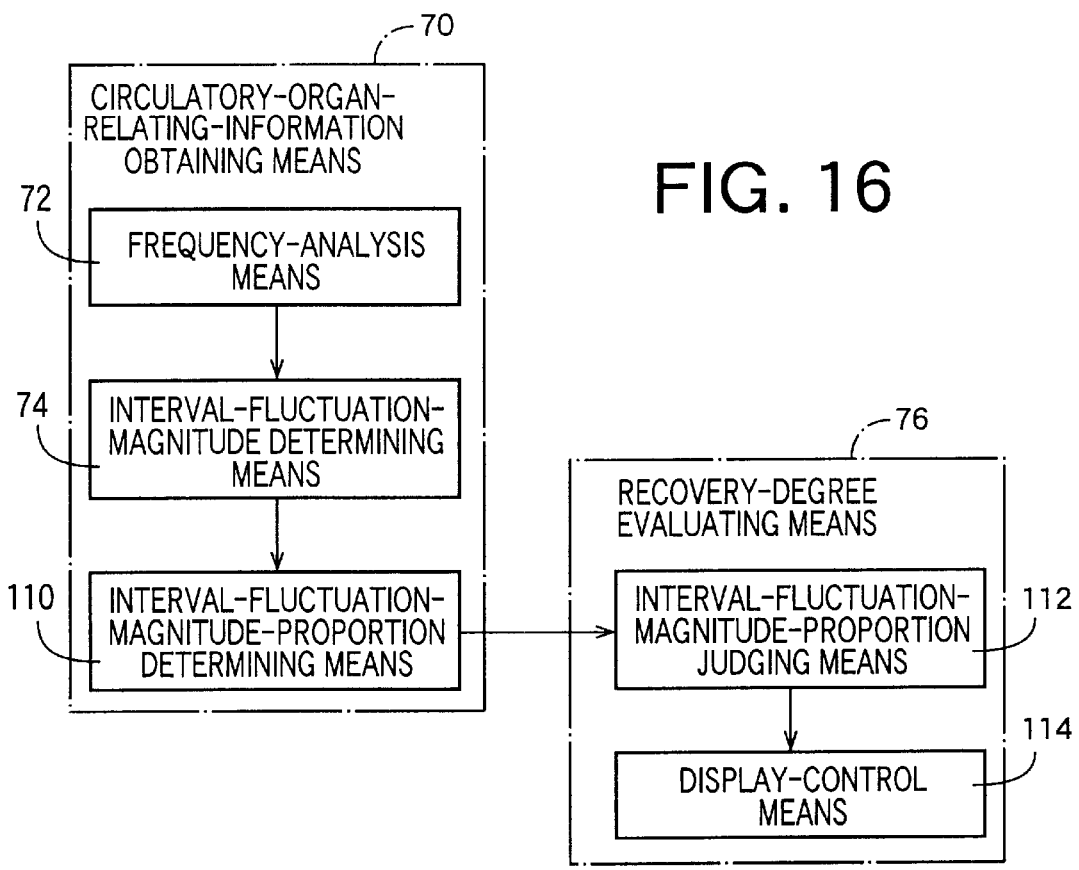
FIG. 16 is a block diagram corresponding to FIG. 2, for explaining essential functions of an electronic control device of another living-subject monitoring apparatus as a fourth embodiment of the present invention.

FIG. 16 is a block diagram for explaining essential functions of the electronic control device 28 of the present living-subject monitoring apparatus as the fourth embodiment, including a recovery-degree evaluating function. In the figure, a circulatory-organ-relating-information obtaining means 70 iteratively obtains, as a sort of information relating to circulatory organ of a living subject, a low-frequency interval-fluctuation-magnitude proportion $R_P$, i.e., a proportion, $P_L/P_T$, of a low-frequency interval fluctuation magnitude $P_L$, shown in FIG. 17, with respect to a whole-frequency fluctuation magnitude $P_T$, of a frequency spectrum obtained from the heart rate values HR determined based the ECG signal $SM_2$ supplied from the ECG device 34, and/or a high-frequency interval-fluctuation-magnitude proportion $R_P$, i.e., a proportion, $P_H/P_T$, of a high-frequency interval fluctuation magnitude $P_H$ with respect to the whole-frequency fluctuation magnitude $P_T$ of the frequency spectrum. To this end, the information obtaining means 70 includes a frequency-analysis means 72, an interval-fluctuation-magnitude determining means 74, and an interval-fluctuation-magnitude-proportion determining means 110. The interval-fluctuation-magnitude-proportion determining means 110 iteratively determines a low-frequency interval-fluctuation-magnitude proportion $R_P$ (=$P_L/P_T$) as the proportion of a low-frequency interval fluctuation magnitude $P_L$, determined by the interval-fluctuation-magnitude determining means 74, with respect to a whole-frequency fluctuation magnitude $P_T$, of a frequency spectrum, obtained by the frequency-analysis means 72, from the heart rate values HR, and/or a high-frequency interval-fluctuation-magnitude proportion $R_P$ (=$P_H/P_T$) as the proportion of a high-frequency interval fluctuation magnitude $P_H$, determined by the means 74, with respect to the whole-frequency fluctuation magnitude $P_T$ of the frequency spectrum.

A recovery-degree evaluating means 76 evaluates, based on each of the low-frequency and/or high-frequency interval-fluctuation-magnitude proportions $P_L/P_T$, $P_H/P_T$ iteratively determined by the circulatory-organ-relating-information obtaining means 70, a degree of recovery of a living subject from a surgical operation. To this end, the evaluating means 76 includes an interval-fluctuation-magnitude-proportion judging means 112 and a display-control means 114. The interval-fluctuation-magnitude-proportion judging means 102 judges whether each of the low-frequency interval-fluctuation-magnitude-proportion values $P_L/P_T$ is greater than a prescribed reference value $Y_{L1}$ and/or judges whether the high-frequency interval-fluctuation-magnitude-proportion values $P_H/P_T$ is greater than a prescribed reference value $Y_{H1}$. And, if a positive judgment is made, the judging means 112 judges that the living subject has recovered from the surgical operation. It is speculated that the interval-fluctuation-magnitude proportion $P_L/P_T$, $P_H/P_T$ is an amount which closely reflects the degree of activity of the sympathetic nerve system of the subject. Thus, the present monitoring apparatus evaluates the degree of recovery of the living subject from the surgical operation, by judging whether the activity of the sympathetic nerve system of the subject has become stable. FIG. 17 is a graph for explaining the interval-fluctuation-magnitude proportion $P_L/P_T$, $P_H/P_T$, for example, the low-frequency interval-fluctuation-magnitude proportion $P_L/P_T$ as the proportion of a low-frequency fluctuation magnitude $P_L$, i.e., an area hatched by solid lines, enveloped by a portion of the frequency spectrum in a prescribed low-frequency interval corresponding to a low-frequency peak L, with respect to a whole-frequency fluctuation magnitude $P_T$, i.e., an area hatched by broken lines, enveloped by the whole frequency spectrum in the whole frequency range. The display-control means 114 operates the display device 32 to display a message or a color, or light a lamp, indicating the positive or negative judgment made by the interval-fluctuation-magnitude-proportion judging means 112.

Figure 18:
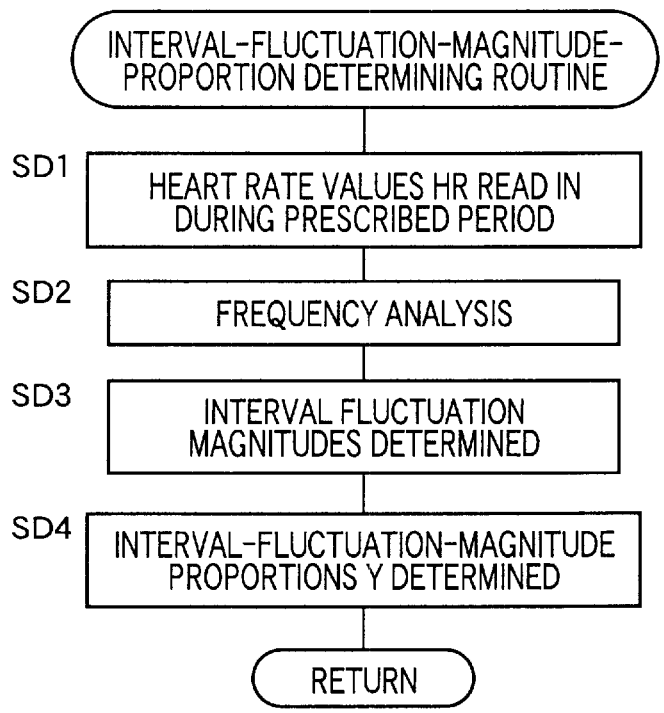
FIG. 18 is a flow chart representing an interval-fluctuation-magnitude-proportion determining routine according to which the control device of FIG. 16 determines an interval-fluctuation-magnitude proportion.
Figure 19:
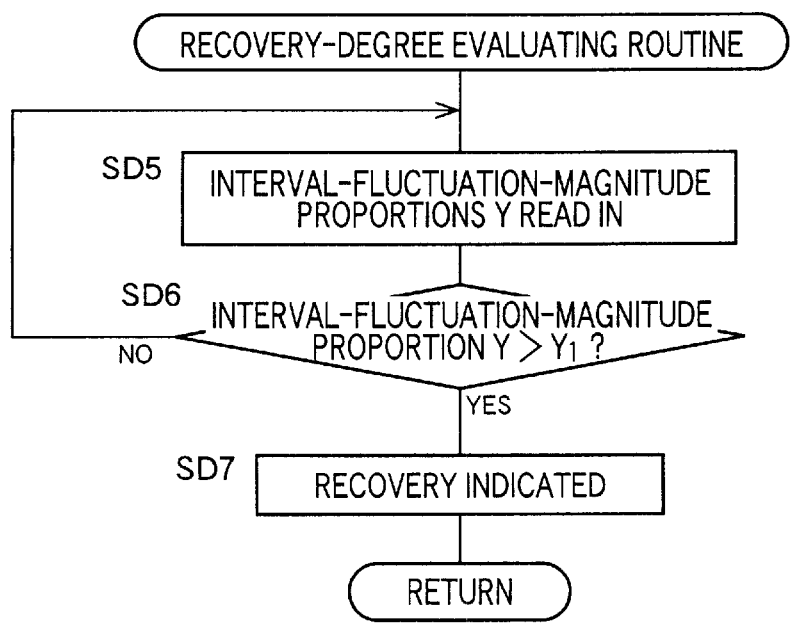
FIG. 19 is a flow chart representing a recovery-degree evaluating routine according to which the control device of FIG. 16 evaluates a degree of recovery of a living subject.

Next, there will be described a recovery-degree evaluating operation of the electronic control device 28 of the fourth monitoring apparatus, by reference to the flow charts of FIGS. 18 and 19. FIG. 18 shows an interval-fluctuation-magnitude-proportion determining routine, and FIG. 19 shows a recovery-degree evaluating routine. At Step SD1 (hereinafter, "Step" is omitted), SD2 corresponding to the frequency-analysis means 72, and SD3 corresponding to the interval-fluctuation-magnitude determining means 74, the control device 28 operates like at SA1, SA2, and SA3 of FIG. 7, that is, reads in the heart rate values HR, subjects the heart rate values HR to the frequency analysis, and iteratively determines, based on the obtained frequency spectrum, a low-frequency fluctuation magnitude $P_L$ corresponding to a flow-frequency peak L in a prescribed low-frequency interval, and a high-frequency fluctuation magnitude $P_H$ corresponding to a flow-frequency peak H in a prescribed high-frequency interval. Then, at SD4 corresponding to the interval-fluctuation-magnitude-proportion determining means 110, the control device 28 iteratively determines a proportion $P_L/P_T$ of the low-frequency fluctuation magnitude $P_L$, determined at SD3, i.e., an area enveloped by a portion of the frequency distribution in a prescribed low-frequency interval, hatched by solid lines in FIG. 17, with respect to a whole fluctuation magnitude $P_T$, i.e., an area enveloped by the whole frequency distribution in the whole frequency band, hatched by broken lines in FIG. 17, and/or a proportion $P_H/P_T$ of the high-frequency fluctuation magnitude $P_H$, determined at SD3, i.e., an area enveloped by a portion of the frequency distribution in a prescribed high-frequency interval, with respect to the whole fluctuation magnitude $P_T$.

At SD5 of FIG. 19, the control device 28 reads in the low-frequency and/or high-frequency interval-fluctuation-magnitude proportions $P_L/P_T$, $P_H/P_T$ determined at SD4. Next, at SD6 corresponding to the interval-fluctuation-magnitude-proportion judging means 112, the control device 28 judges whether the low-frequency interval-fluctuation-magnitude proportion $P_L/P_T$ read in at SD5 is greater than a prescribed reference value $Y_{L1}$, and/or judges whether the high-frequency interval-fluctuation-magnitude proportion $P_H/P_T$ read in at SD5 is greater than a prescribed reference value $Y_{H1}$, Each of the reference values $Y_{L1}$, $Y_{H1}$ is experimentally obtained as a value indicating that the activity of the sympathetic and parasympathetic nerve systems of the living subject after the surgical operation has increased to not smaller than a certain value and accordingly the subject has recovered from the operation. If a negative judgment is made at SD6, the control device 28 repeats SD5 and SD6. Meanwhile, if a positive judgment is made at SD6, the control goes to SD7 corresponding to the display-control means 114, where the control device 28 operates the display device 32 to indicate that the subject has recovered from the operation.

It is speculated that the low-frequency or high-frequency interval-fluctuation-magnitude proportion $P_L/P_T$, $P_H/P_T$ faithfully reflects the activity of the autonomic nerve system of the subject. The present monitoring apparatus evaluates the degree of recovery of the subject, by judging whether the low-frequency or high-frequency interval-fluctuation-magnitude proportion $P_L/P_T$, $P_H/P_T$ is greater than the prescribed low-pressure or high-pressure reference value $Y_{L1}$, $Y_{H1}$. Thus, the present monitoring apparatus can objectively and accurately evaluate the degree of recovery of the subject.

Figure 20:
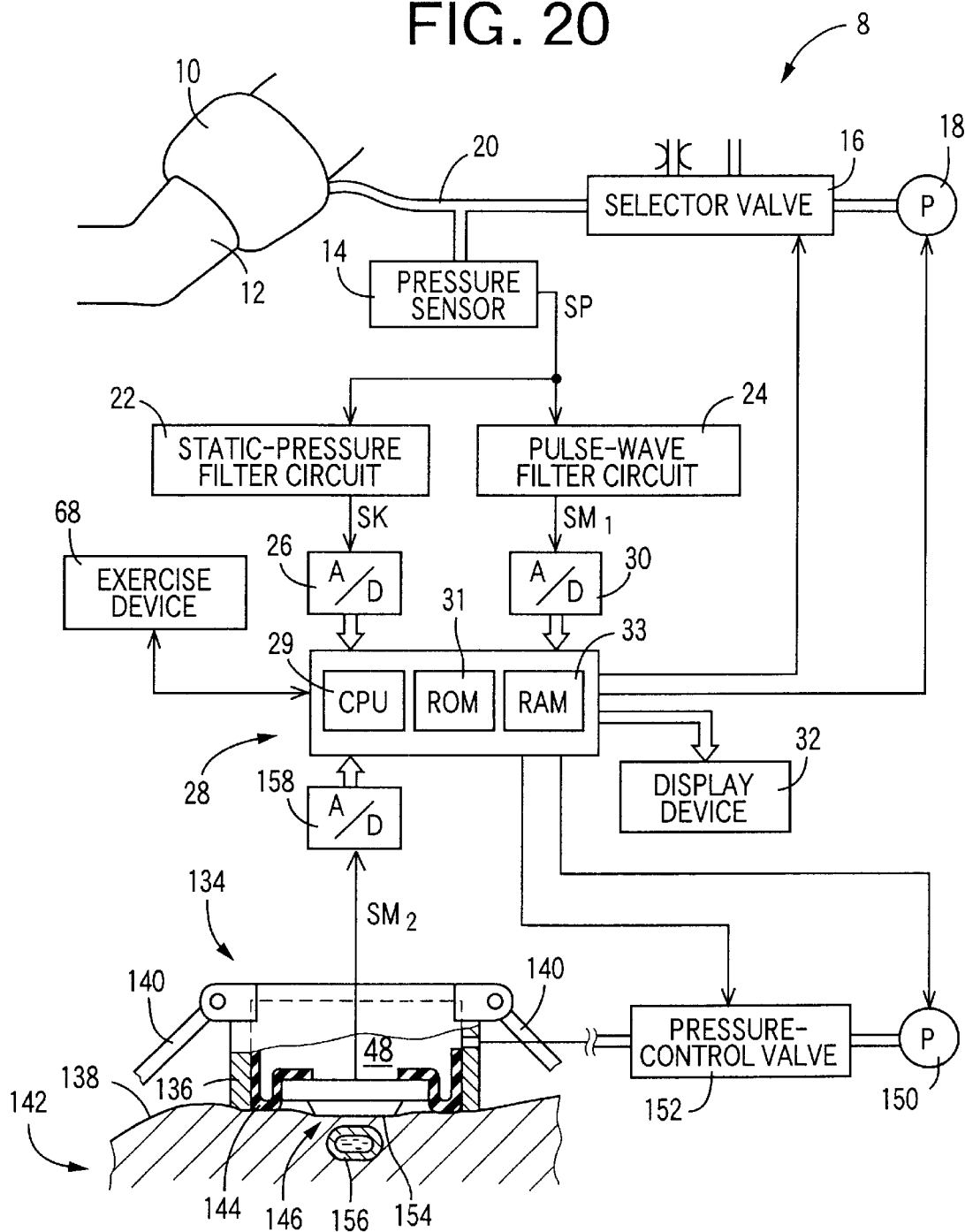
FIG. 20 is a diagrammatic view for explaining an apparatus which iteratively measures a blood pressure value as a sort of circulatory-organ-relating information, and to which the present invention is applied.

In the first to fourth embodiments, the interval fluctuation magnitude $P_L$, $P_H$ of the heart rate values HR, the interval-fluctuation-magnitude ratio $P_L/P_H$ of the heart rate values HR, the sharpness degree $K_L$, $K_H$ of waveform of fluctuation peak of the frequency spectrum of the heart rate values HR, or the interval-fluctuation-magnitude proportion $P_L/P_T$, $P_H/P_T$ of the heart rate values HR is iteratively obtained as a sort of circulatory-organ-relating information. However, it is possible to replace one or more of those sorts of circulatory-organ-relating information with one or more of a heart rate value HR, a blood pressure value, an interval fluctuation magnitude or magnitudes of iteratively obtained blood pressure values, an interval-fluctuation-magnitude ratio of the blood pressure values, a sharpness degree of a waveform of a fluctuation peak or peaks of a frequency spectrum of the blood pressure values, or an interval-fluctuation-magnitude proportion or proportions of the blood pressure values. The interval fluctuation magnitude or magnitudes of the blood pressure values, the interval-fluctuation-magnitude ratio of the blood pressure values, the sharpness degree of waveform of fluctuation peak or peaks of frequency spectrum of the blood pressure values, or the interval-fluctuation-magnitude proportion or proportions of the blood pressure values may be iteratively obtained by replacing the ECG device 34 employed in the first to fourth embodiments shown in FIGS. 2 to 19, with, e.g., a pressure-pulse-wave detecting probe 134, as shown in FIG. 20. It is known that each of blood pressure values BP, heart rate values HR, or fluctuation magnitude of blood pressure values which are obtained from a living subject after a surgical operation has such a tendency (or nature) to change toward its value before the operation and become stable around a saturation value.

FIG. 20 shows an apparatus which iteratively obtains, from a living subject, a blood pressure value as a sort of circulatory-organ-relating information, and to which the present invention is applied. In FIG. 20, the pressure-pulse-wave detecting probe 134 includes a container-like housing 136 which is detachably attached, with fastening bands 140, to a body surface 138 of a wrist 142 on an artery-downstream side of an upper arm 12 of a patient around which an inflatable cuff 10 is worn, such that an opening end of the housing 136 is opposed to the body surface 138. In addition, the probe 134 includes a pressure-pulse-wave sensor 146 which is secured via a diaphragm 144 to an inner wall of the housing 136, such that the sensor 146 is movable relative to the housing 136 and is advanceable out of the opening of the same 136. The housing 136, the diaphragm 144, etc. cooperate with one another to define a pressure chamber 148, which is supplied with a pressurized air from an air pump 150 via a pressure-control valve 152 so that an air pressure in the pressure chamber 148 is held at an optimum pressing pressure PHDP. Thus, the pressure-pulse-wave sensor 146 is pressed against the body surface 138 with a pressing force PHD corresponding to the air pressure in the pressure chamber 148.

The pressure-pulse-wave sensor 146 includes a semiconductor chip provided by, e.g., a monocrystalline silicon, and having a flat press surface 154, and a number of semiconductor pressure sensing elements (not shown) arranged on the press surface 154. The sensor 146 is pressed against the body surface 138 right above a radial artery 156 of the wrist 142, to detect a pressure pulse wave, i.e., a pressure oscillation which is produced from the radial artery 156 and is transmitted to the body surface 138, and supplies a pressure-pulse-wave signal $SM_2$ to an electronic control device 28 via an A/D converter 158.

A CPU 29 of the control device 28 outputs drive signals to the air pump 150 and the pressure-control valve 152, and thereby controls the air pressure in the pressure chamber 148, i.e., the pressing force applied by the sensor 146 to the skin 138, according to control programs pre-stored in a ROM 31. In a continuous pressure-pulse-wave measuring operation, the control device 28 determines, based on the pressure pulse wave continuously detected by the sensor 146 while the pressure in the pressure chamber 148 is changed, an optimum pressing pressure PHDP at which the sensor 146 is pressed against the radial artery 156 such that a portion of the wall of the artery 156 is flattened. The control device 28 controls the pressure-control valve 152 so as to maintain the pressure of the pressure chamber 148 at the thus determined optimum pressing pressure $P_{HDP}$. In addition, the control device 28 determines a relationship between blood pressure and pressure-pulse-wave magnitude $P_M$, based on at least two of an upper-peak magnitude $P_{Hpk}$ of the pressure pulse wave detected by the sensor 146, a magnitude of a gravity center of an area enveloped by the pressure pulse wave, and a lower-peak magnitude $P_{Lpk}$ of the pressure pulse wave, and at least corresponding two of a systolic blood pressure value $P_{BPSYS}$ measured using the cuff 10 according to an oscillometric method, a mean blood pressure value $P_{BPMEAN}$ measured using the cuff 10, and a diastolic blood pressure value $P_{BPDIA}$ measured using the cuff 10. Moreover, the control device 28 iteratively determines, according to the thus determined relationship, a blood pressure value based on an upper peak and/or a lower peak of each of heartbeat-synchronous pulses of the pressure pulse wave detected by the sensor 146. That is, the magnitude of pressure pulse wave detected by the sensor 146 is calibrated by the determination of relationship, and the thus calibrated pressure pulse wave provides a continuous blood-pressure waveform indicating instantaneous blood pressure values in the artery. Thus, the magnitude of each upper peak of the continuous blood-pressure waveform represents a systolic blood pressure value, and the magnitude of each lower peak of the continuous blood-pressure waveform represents a diastolic blood pressure value. The above-indicated relationship may be expressed by, e.g., $P_{BP}=A \times PM+B$, where A is a constant indicating a slope, and B is a constant indicating an intercept.

While the present invention has been described in its preferred embodiments by reference to the drawings, it is to be understood that the invention may otherwise be embodied.

For example, in the first embodiment shown in FIGS. 2 to 8, the fluctuation magnitude of the heart rate values HR is employed as the circulatory-organ-relating information. However, it is possible to employ, in place of the fluctuation magnitude of the heart rate values HR, a blood pressure value BP, a heart rate value HR, a heart period value $T_{RR}$, or a central frequency of a fluctuation of blood pressure values BP, heart rate values HR, or heart period values $T_{RR}$, as the circulatory-organ-relating information. In the latter cases, the circulatory-organ-relating-information obtaining means 70 may be provided by the continuous blood-pressure measuring apparatus shown in FIG. 20, or a means which determines a heart rate value HR based on the ECG detected by the ECG device 34, the cuff pulse wave detected from the cuff 10, or the photoelectric pulse wave detected by the photoelectric-pulse-wave detecting probe 38 for use with the pulse oximeter.

In addition, in each of the illustrated embodiments, the recovery-degree evaluating means 76 displays the result of judgment on the display device 32. However, it is possible to display, in digits or in a graph, a value as the circulatory-organ-relating information, together with a reference value for the information, so that the degree of recovery of the living subject can be evaluated by the subject or the doctor based on the displayed digits or graph.

It is to be understood that the present invention may be embodied with other changes, improvements, and modifications that may occur to a person skilled in the art without departing from the spirit and scope of the invention defined in the appended claims.

What is claimed is:

1. An apparatus for evaluating a degree of recovery of a living subject from a surgical operation which the subject has undergone, the apparatus comprising:
   a circulatory-organ-relating-information obtaining means for iteratively obtaining, after the operation, a piece of circulatory-organ-relating information relating to a circulatory organ of the subject; and
   a recovery-degree evaluating means for evaluating the degree of recovery of the subject, based on at least one piece of circulatory-organ-relating information obtained by the circulatory-organ-relating-information obtaining means.

2. An apparatus according to claim 1, wherein the recovery-degree evaluating means comprises means for evaluating the degree of recovery of the subject, by judging whether a change of a plurality of pieces of circulatory-organ-relating information iteratively obtained by the circulatory-organ-relating-information obtaining means is smaller than a reference value and accordingly is stable.

3. An apparatus according to claim 1, wherein the circulatory-organ-relating-information obtaining means comprises means for iteratively obtaining, as a piece of circulatory-organ-relating information, one selected from the group consisting of a blood pressure value, a heart rate value, a fluctuation of blood pressure values, and a magnitude of a fluctuation of heart rate values.

4. An apparatus according to claim 1, wherein the recovery-degree evaluating means comprises means for determining a saturation value based on a time-wise change of a plurality of pieces of circulatory-organ-relating information iteratively obtained by the circulatory-organ-relating-information obtaining means, means for determining, based on the saturation value, a reference value smaller than the saturation value, and means for evaluating the degree of recovery of the subject, by judging whether a piece of circulatory-organ-relating information obtained by the circulatory-organ-relating-information obtaining means is greater than the reference value.

5. An apparatus according to claim 1, wherein the circulatory-organ-relating-information obtaining means comprises means for iteratively obtaining, as a piece of circulatory-organ-relating information, one selected from the group consisting of a magnitude of a low-frequency fluctuation of blood pressure values, and a ratio of one of a magnitude of a low-frequency fluctuation of heart rate values and a magnitude of a high-frequency fluctuation of the heart rate values to the other of the magnitude of low-frequency fluctuation of heart rate values and the magnitude of high-frequency fluctuation of heart rate values, and wherein the recovery-degree evaluating means comprises means for evaluating the degree of recovery of the subject, by judging whether said one selected from the group is greater than a reference value.

6. An apparatus according to claim 1, wherein the circulatory-organ-relating-information obtaining means comprises means for iteratively obtaining, as a piece of circulatory-organ-relating information, one selected from the group consisting of a frequency distribution of fluctuations of blood pressure values, and a frequency distribution of fluctuations of heart rate values, and means for determining a degree of sharpness of said one selected from the group, and wherein the recovery-degree evaluating means comprises means for evaluating the degree of recovery of the subject, by judging whether the determined degree of sharpness is greater than a reference value.

7. An apparatus according to claim 1, wherein the circulatory-organ-relating-information obtaining means comprises means for iteratively obtaining, as a piece of circulatory-organ-relating information, one selected from the group consisting of a frequency spectrum of fluctuations of blood pressure values, and a frequency spectrum of fluctuations of heart rate values, and means for determining a proportion of an interval fluctuation magnitude of said one selected from the group in a prescribed frequency interval, with respect to a whole fluctuation magnitude of said one selected from the group in a whole frequency range, and wherein the recovery-degree evaluating means comprises means for evaluating the degree of recovery of the subject, by judging whether the determined proportion is greater than a reference value.

8. An apparatus according to claim 1, wherein the recovery-degree evaluating means comprises means for evaluating the degree of recovery of the subject, by judging whether a piece of circulatory-organ-relating information obtained by the circulatory-organ-relating-information obtaining means falls within a reference range.

9. An apparatus according to claim 1, wherein the circulatory-organ-relating-information obtaining means comprises means for iteratively obtaining, as a piece of circulatory-organ-relating information, one selected from the group consisting of a ratio of one of a magnitude of a low-frequency fluctuation of blood pressure values and a magnitude of a high-frequency fluctuation of the blood pressure values to the other of the magnitude of low-frequency fluctuation of blood pressure values and the magnitude of high-frequency fluctuation of blood pressure values, and a ratio of one of a magnitude of a low-frequency fluctuation of heart rate values and a magnitude of a high-frequency fluctuation of the heart rate values to the other of the magnitude of low-frequency fluctuation of heart rate values and the magnitude of high-frequency fluctuation of heart rate values.

10. An apparatus according to claim 1, wherein the circulatory-organ-relating-information obtaining means comprises means for iteratively obtaining, as a piece of circulatory-organ-relating information, one selected from the group consisting of a frequency of a peak of a frequency distribution of fluctuations of blood pressure values, and a frequency of a peak of a frequency distribution of fluctuations of heart rate values.

11. An apparatus according to claim 1, wherein the circulatory-organ-relating-information obtaining means comprises means for iteratively obtaining, as a piece of circulatory-organ-relating information, one selected from the group consisting of an area enveloped by a frequency distribution of fluctuations of blood pressure values in a prescribed frequency interval, and an area enveloped by a frequency distribution of fluctuations of heart rate values in a prescribed frequency interval.

12. An apparatus according to claim 1, wherein the circulatory-organ-relating-information obtaining means comprises means for iteratively obtaining, as a piece of circulatory-organ-relating information, one selected from the group consisting of an area enveloped by a frequency spectrum of fluctuations of blood pressure values in a prescribed frequency interval, and an area enveloped by a frequency spectrum of fluctuations of heart rate values in a prescribed frequency interval, and means for determining a proportion of said one selected from the group, with respect to an area enveloped by the whole frequency spectrum in a whole frequency range, and wherein the recovery-degree evaluating means comprises means for evaluating the degree of recovery of the subject, by judging whether the determined proportion is greater than a reference value.

* * * * *